(12) United States Patent
Ziv et al.

(10) Patent No.: US 7,670,590 B2
(45) Date of Patent: *Mar. 2, 2010

(54) PERTURBED MEMBRANE-BINDING COMPOUNDS AND METHODS OF USING THE SAME

(75) Inventors: Ilan Ziv, Kfar Saba (IL); Anat Shirvan, Herzliya (IL)

(73) Assignee: Aposense Ltd., Petach-Tikva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 11/882,490

(22) Filed: Aug. 2, 2007

(65) Prior Publication Data

US 2008/0014148 A1 Jan. 17, 2008

Related U.S. Application Data

(62) Division of application No. 10/799,586, filed on Mar. 15, 2004, now Pat. No. 7,270,799.

(60) Provisional application No. 60/536,493, filed on Jan. 15, 2004, provisional application No. 60/537,289, filed on Jan. 20, 2004.

(51) Int. Cl.
*A61K 51/00* (2006.01)
*A61K 49/04* (2006.01)

(52) U.S. Cl. .................. 424/1.11; 424/9.364; 424/9.4

(58) Field of Classification Search .......... 424/9.3, 424/9.37, 9.4; 514/1, 562
See application file for complete search history.

(56) References Cited

U.S. PATENT DOCUMENTS 4,578,503 A 3/1986 Ishikawa et al.

FOREIGN PATENT DOCUMENTS

| GB | 1401579 | 7/1975 |
| WO | WO02/46147 | * 6/2002 |

OTHER PUBLICATIONS

Peggy L. Olive, John E. Biaglow, Marie E. Varnes and Ralph E. Durand, Characterization of the Uptake and Toxicity of a Fluorescent Thiol Reagent, Cytometry, vol. 3(5), 349-353, 1982.*

Peggy L. Olive, John E. Biaglow, Marie E. Varnes and Ralph E. Durand, Characterization of the Uptake and Toxicity of a Fluorescent Thiol Reagent, Cytometry, vol. 3(5), 349-353, 1982.*

Stubbe et al., "Are Carboxylations Involving Biotin Concerted or Nonconcerted?", The Journal of Biological Chemistry, vol. 255, No. 1, (1980), pp. 236-242.

Peggy L. Olive et al. Characterization of the Uptake and Toxicity of a Fluorescent Thiol Reagent Cytometry by the Society for Analytical Cytology pp. 349-353 vol. 3, No. 5, Jul. 12, 1982 The John Hopkins Oncology Center, Section of Radiobiology, Baltimore, Maryland USA & Dept. of Radiology, Case Western Reserve University, Cleveland, Ohio, USA.

* cited by examiner

*Primary Examiner*—Michael G Hartley
*Assistant Examiner*—Jagadishwar R Samala
(74) *Attorney, Agent, or Firm*—Pearl Cohen Zedek Latzer, LLP

(57) ABSTRACT

The present invention relates to compounds that selectively bind to cells undergoing perturbations and alterations of their normal plasma membrane organization, such as cells undergoing apoptosis or activated platelets. The invention further provides methods for utilizing said compounds in medical practice, for diagnostic and therapeutic purposes.

10 Claims, 5 Drawing Sheets

Figure 2

Table 1

| Brain hemisphere | NST200 uptake (%ID/g +SEM) | Ratio damaged/control hemisphere | Region of interest (ROI); Signal to background ratio |
|---|---|---|---|
| Damaged (1 hour) | 0.1854 ± 0.05 | 1.84 | 6.13 |
| Control (1 hour) | 0.1006 ± 0.01 | | |
| Damaged (2 hours) | 0.0543 ± 0.004 | 2.02 | 6.73 |
| Control (2 hours) | 0.0269 ± 0.002 | | |

1

PERTURBED MEMBRANE-BINDING COMPOUNDS AND METHODS OF USING THE SAME

CROSS REFERENCE DATA

This application is a divisional application from U.S. patent application Ser. No. 10/799,586, filed Mar. 15, 2004 now U.S. Pat. No. 7,270,799, which claims priority from both of U.S. Provisional Application No. 60/536,493, filed Jan. 15, 2004 and U.S. Provisional Application No. 60/537,289, filed Jan. 20, 2004, all of which are incorporated herein by reference.

FIELD OF THE INVENTION

The invention relates to compounds that selectively bind to cells undergoing perturbations and alterations of their normal plasma membrane organization, i.e., cells undergoing cell death, apoptotic cells or activated platelets. The invention further provides methods for utilizing said compounds in medical practice, for diagnostic and therapeutic purposes.

BACKGROUND OF THE INVENTION

The plasma membrane (outer membrane) of intact eukaryotic cells is characterized by a highly organized structure. This high level of membrane organization is determined, among others, by the molecular structure of the specific lipids constituting the membrane; the ratio between the various lipid species from which the membrane is composed; the distribution of the phospholipids between the outer and inner leaflets of the membrane; and by the membrane protein constituents.

While maintenance of the high level of plasma membrane organization is fundamental to normal cell physiology, substantial perturbations and alterations of the normal organization of the cell plasma membrane (PNOM) occur in numerous physiological and pathological conditions, and are characterizing a plurality of diseases. Such alterations and perturbations may be evident both at the morphological level (membrane blebbing observed in cells undergoing apoptosis) and at the molecular level. The scope of perturbations accompanying either cell death, cell disease or cell activation, is not fully elucidated. They include, among others, scrambling and redistribution of the membrane phospholipids, with movement to the cell surface of aminophsopholipids, mainly phosphatidylserine (PS) and phosphatidylethanolamine (PE), which are normally restricted almost entirely to the inner leaflet of the membrane bilayer, and reciprocal movement of sphingomyelin (SM) and phosphatidylcholine (PC) from the outer leaflet to the inner leaflet of the membrane. This redistribution is referred herein as loss of cell membrane lipid asymmetry (CMLA). In addition to PNOM, CMLA loss is also often associated with reduction in the level of packing of membrane phospholipids and an increase in membrane fluidity.

These alterations play an important role in rendering the cell surface a catalytic platform for the assembly of several clotting factor complexes, such as the tenase and prothrombinase protein complexes. Accordingly, platelet activation is associated with platelet membrane undergoing PNOM, and these alterations constitute an important factor in normal blood coagulation, as well as in the initiation and/or propagation of abnormal, excessive blood clotting in numerous disorders. These disorders include, among others, arterial or venous thrombosis or thromboembolism [e.g., cerebral stroke, myocardial infarction, deep vein thrombosis (DVT), disseminated intravascular coagulation (DIC), thrombotic thrombocytopenic purpura, etc.], unstable atherosclerotic plaques, sickle cell disease, beta-thalassemia, anti-phospholipid antibody syndrome [among others in systemic lupus erythematosus (SLE)], and disorders associated with shedding of membrane microparticles, e.g., neurological dysfunction in association with cardiopulmonary bypass.

Apoptosis is another major situation in which alterations/perturbations of cell membrane take place. Apoptosis is an intrinsic program of cell self-destruction or "suicide", which is inherent in every eukaryotic cell. In response to a triggering stimulus, cells undergo a highly characteristic cascade of events of cell shrinkage, blebbing of cell membranes, chromatin condensation and fragmentation, culminating in cell conversion to clusters of membrane-bound particles (apoptotic bodies), which are thereafter engulfed by macrophages. PNOM is a universal phenomenon of apoptosis, it occurs early in the apoptotic cascade, probably at the point of cell commitment to the death process, and has also been shown to be an important factor in the recognition and removal of apoptotic cells by macrophages.

A strong correlation has been recently drawn between PNOM and a potent procoagulant activity of apoptotic cells. PNOM in apoptotic endothelial cells, such as those occurring in atherosclerotic plaques, probably plays an important role in the pathogenesis of thrombotic vascular disorders.

Since apoptosis or thrombosis has an important role in the majority of medical disorders, it is desirable to have tools for detection of these biological processes and targeting of associated cells. Compounds for selective binding to PNOM membranes, potentially also performing subsequent entry into these cells having such PNOM membranes (PNOM-cells), may therefore serve as an important tool for detecting and targeting of drugs to cells undergoing damage or death process, especially by apoptosis, or platelets undergoing activation.

SUMMARY OF THE INVENTION

In an embodiment of the invention, there are provided compounds that can selectively bind to cells undergoing perturbation of their normal organization of the plasma membrane (PNOM-cells), while binding to a much lesser degree to cells, which maintain the normal organization of their plasma membrane. The ratio of binding is at least 30% higher in the PNOM-cell in comparison to a cell which maintains the normal organization of its plasma membrane, and which is defined hereto as a "normal cell". The PNOM-cells are in one embodiment of the invention cells undergoing a death process, in another embodiment they are apoptotic cells and in another embodiment they are activated platelets. The invention further relates to methods of detecting PNOM-cells by using these compounds, which selectively bind to the PNOM-cells. In another embodiment of the invention, compounds are provided, represented, by any of the structure set forth in formulae II-XII.

The term "perturbed membrane-binding compound" (PMBC) refers to a compound that selective targets PNOM-cells, while binding to a lesser degree to normal cells. According to the invention, binding of the PMBC to the PNOM-cell should be a least 30% greater than its binding to the normal cell.

The term "selective targeting" refers in the invention to the selective binding of a compound to PNOM-cells, i.e., binding to the PNOM-cell in an extent which is at least 30% greater than binding to normal cells.

The term "diagnostic perturbed membrane-binding compound" (diagnostic PMBC) refers to a compound capable of selective targeting to PNOM-cells, wherein said compound comprises or is linked to a marker, said marker being detectable by means known to those skilled in the art.

The term "therapeutic perturbed membrane-binding compound" (therapeutic PMBC) refers to a PMBC as defined above, comprising a drug, useful in the treatment of disease.

The term "solid support" refers in the contents of the present invention to a solid matrix, an insoluble matrix, and an insoluble support. The solid support in accordance with the present invention may be formed in a variety of structures such as a stack of micro-particulates, micro-filters, or micro-capillara, and may be composed of various materials such as alumina, diatomaceous earth, celite, calcium carbonate, calcium sulfate, ion-exchange resin, silica gel, charcoal, amberlite, Dowex, Eupergit and ethylsufoxycellulose.

The PMBC is used in an embodiment of the invention for the preparation of an agent for selective targeting cells, which have perturbed membranes.

In one aspect, the present invention provides a compound which selectively binds to a PNOM-cell (i.e., a PMBC), said compound having the structure set forth in formula (I):

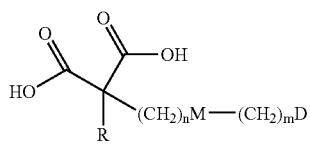

(I)

or pharmaceutically acceptable salts, metal chelates, solvates and hydrates of the compound represented by the structure as set forth in formula (I), and solvates and hydrates of said salts; wherein, R represents hydrogen, $C_1, C_2, C_3, C_4, C_5, C_6, C_7, C_8, C_9, C_{10} C_{11}, C_{12}, C_{13}, C_{14}$ linear or branched alkyl, linear or branched hydroxyl-alkyl, linear or branched fluoro-alkyl, one or two-ring aryl or heteroaryl, or combinations thereof; n and m each stands for an integer of 0, 1, 2, 3 or 4, n and m can be the same or different; M is selected from null, —O—, —S—, —C(O)NH—, and —N(U)—, wherein U stands for a null, hydrogen, $C_1, C_2, C_3$, or $C_4$ alkyl, or $C_1, C_2, C_3$, or $C_4$ alkylene; D is selected from hydrogen, a drug to be targeted to the PNOM-cell and a marker for diagnostics selected from a marker for imaging and a metal chelate; the marker for imaging may be detected by color, fluorescence, x-ray, CT scan, magnetic resonance imaging (MRI) or radio-isotope scan such as single photon emission tomography (SPECT) or positron emission tomography (PET); wherein the above alkylene groups bound to M or D, or the aryl or heteroaryl of R may each be substituted at each occurrence by a group selected from anino, F, $NO_2$, OH and SH.

The drug (i.e., D) may be a medicinally-useful agent for the prevention, amelioration, or treatment of a specific disease and may be, for example, without being limited: an inhibitor of apoptosis, (e.g., a caspase inhibitor, antioxidant, modulator of the Bcl-2 system); an activator of cell death (e.g. an anti-cancer drug); or a modulator of blood coagulation, which may be an anticoagulant, an antithrombotic, or a thrombolytic agent. In such case, said drug may be selected among an antiplatelet agent, heparin, low molecular weight heparin, antagonists of glycoprotein IIb/IIIa, tissue plasminogen activator (tPA), or an inhibitor of a clotting factor, such as an inhibitor of thrombin or an inhibitor of factor Xa; or an anti-inflammatory drug or an immuno-modulatory drug. In another embodiment, D maybe a metal chelate.

In another embodiment of the invention, D may be a solid support.

In another embodiment of the invention there is provided a compound which selectively targets a PNOM-cell, said compound being represented by the structure as set forth in formula (II):

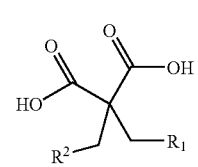

II including pharmaceutically acceptable salts hydrates, solvates and metal chelates of the compound represented by the structure as set forth in formula (II) and solvates and hydrates of said salts; wherein $R^1$ is hydrogen or $C_1, C_2, C_3, C_4, C_5$ or $C_6$ linear or branched alkyl, and $R^2$ is hydrogen or $C_1, C_2, C_3, C_4$, or $C_5$ or $C_6$ linear or branched alkyl, hydroxy-alkyl or fluoro-alkyl.

In another embodiment of the invention, there is provided a compound represented by the structure as set forth in formula (II) including pharmaceutically acceptable salts hydrates, solvates and metal chelates of the compound represented by the structure as set forth in formula (II) and solvates and hydrates of said salts; wherein $R^1$ is hydrogen or $C_1, C_2, C_3, C_4$, or $C_5$ linear or branched alkyl, and $R^2$ is $C_1, C_2, C_3, C_4$, or $C_5$ fluoro-alkyl. In another embodiment of the invention there is provided a compound represented by the structure as set forth in formula (III):

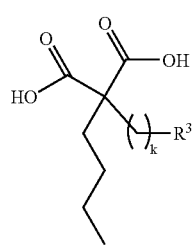

III including pharmaceutically acceptable salts hydrates, solvates and metal chelates of the compound represented by the structure as set forth in formula (III) and solvates and hydrates of said salts; wherein $R^3$ is hydroxyl or F, and k is an integer selected from 1, 2, 3, 4 and 5.

In another embodiment of the invention there is provided a compound represented by the structure as set forth in formula (IV):

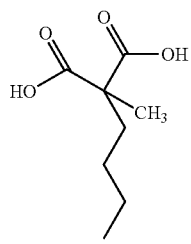

IV including pharmaceutically acceptable salts hydrates, solvates and metal chelates of the compound represented by the structure as set forth in formula (IV) and solvates and hydrates of said salts; said compound is designated NST200.

In another embodiment of the invention there is provided a compound represented by the structure as set forth in formula (V):

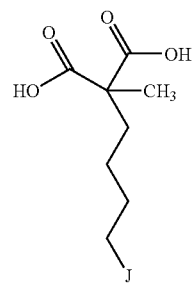

V including pharmaceutically acceptable salts hydrates, solvates and metal chelates of the compound represented by the structure as set forth in formula (V) and solvates and hydrates of said salts; wherein J is selected from —F and —OH. In the case that J is —F, said compound is designated NST201.

In yet another specific embodiment of the invention there is provided a compound represented by the structure as set forth in formula (VI):

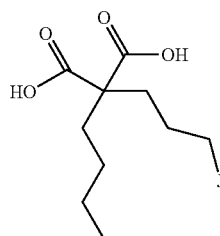

VI including pharmaceutically acceptable salts hydrates, solvates and metal chelates of the compound represented by the structure as set forth in formula (VI) and solvates and hydrates of said salts; wherein J is selected from hydrogen, —F and —OH. In the case that J is —F, said compound is designated NST204.

In another embodiment of the invention there is provided a compound represented by the structure set forth in formula VII:

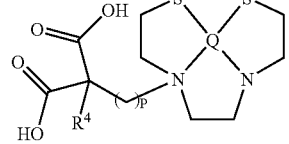

VII including pharmaceutically acceptable salts hydrates, solvates and metal chelates of the compound represented by the structure as set forth in formula (VII) and solvates and hydrates of said salts, wherein Q is selected from Technetium, oxo-Technetium, Rhenium and oxo-Rhenium, $R^4$ is selected from hydrogen, $C_1$, $C_2$, $C_3$, $C_4$, $C_5$, and $C_6$ linear or branched alkyl, and p stands for an integer, selected from 1, 2, 3, 4 and 5.

In another embodiment of the invention there is provided a compound represented by the structure set forth in formula VIII:

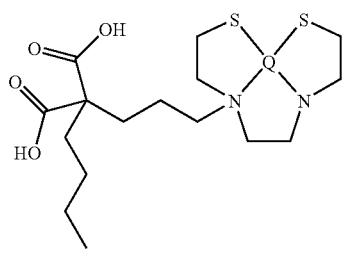

VIII including pharmaceutically acceptable salts hydrates, solvates and metal chelates of the compound represented by the structure as set forth in formula (VIII) and solvates and hydrates of said salts, wherein Q is selected from Technetium, oxo-Technetium, Rhenium and oxo-Rhenium.

In another embodiment of the invention there is provided a compound represented by the structure set forth in formula IX:

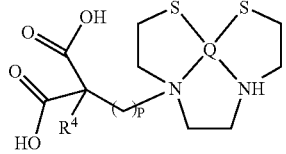

IX including pharmaceutically acceptable salts hydrates, solvates and metal chelates of the compound represented by the structure as set forth in formula (IX) and solvates and hydrates of said salts, wherein Q is selected from Technetium, oxo-Technetium, Rhenium and oxo-Rhenium, $R^4$ is selected from hydrogen, $C_1$, $C_2$, $C_3$, $C_4$, $C_5$, and $C_6$ linear or branched alkyl, and p stands for an integer, selected from 1, 2, 3, 4 and 5.

In another embodiment of the invention there is provided a compound represented by the structure as set forth in formula (X):

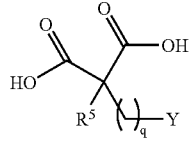

including pharmaceutically acceptable salts hydrates, solvates and metal chelates of the compound represented by the structure as set forth in formula (X) and solvates and hydrates of said salts; wherein $R^5$ is selected from hydrogen, $C_1$, $C_2$, $C_3$, $C_4$, $C_5$, and $C_6$ linear or branched alkyl, $C_1$, $C_2$, $C_3$, $C_4$, $C_5$, and $C_6$ linear or branched fluoro-alkyl, and $C_1$, $C_2$, $C_3$, $C_4$, $C_5$, and $C_6$ linear or branched hydroxy-alkyl; q stands for an integer, selected from 1, 2, 3, 4 and 5; and Y is a marker for fluorescence. In an embodiment of the invention, Y is selected from a dansyl-amide group and fluorescein. In another embodiment of the invention there is provided a compound represented by the structure as set forth in formula (XI):

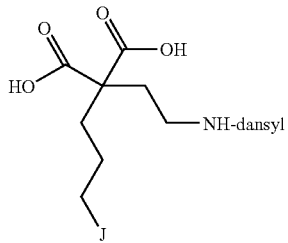

including pharmaceutically acceptable salts hydrates, solvates and metal chelates of the compound represented by the structure as set forth in formula (XI) and solvates and hydrates of said salts; wherein J is selected from hydrogen, methyl, —F and —OH. In the case that J is methyl, the compound is designated NST203.

In another embodiment of the invention there is provided a compound represented by the structure as set forth in formula (XII):

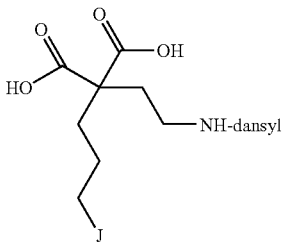

including pharmaceutically acceptable salts hydrates, solvates and metal chelates of the compound represented by the structure as set forth in formula (XII) and solvates and hydrates of said salts; wherein J is selected from hydrogen, methyl, —F and —OH.

In another embodiment of the invention there is provided a compound represented by the structure as set forth in formula (XIII):

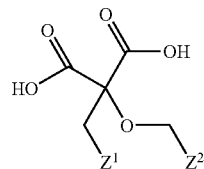

including pharmaceutically acceptable salts hydrates, solvates and metal chelates of the compound represented by the structure as set forth in formula (XIII) and solvates and hydrates of said salts; wherein $Z^1$ and $Z^2$ are each selected from hydrogen and $C_1$, $C_2$, $C_3$, $C_4$, $C_5$ alkyl, hydroxy-alkyl or fluoro-alkyl; Z groups may be the same or different.

In another aspect of the invention, there is provided a pharmaceutical composition for targeting of drugs to foci of apoptosis or blood clotting in a patient, where said patient is a human or non-human mammal, said pharmaceutical composition comprising a compound according to the structure set forth in formulae I, II, III, IV, V, VI, VII, VIII, IX, X, XI XII, or XIII, wherein said compound comprises or is being linked to a drug.

In an aspect of the invention, there is provided a method of selectively targeting a medicinally-useful compound to PNOM-cells being within a population of cells, said method comprising: contacting the cell population with a compound represented by the structure set forth in any one of formulae I, II, III, IV, V, VI, VII, VIII, IX, X, XI, XII or XIII, thereby selectively targeting the medicinally-useful compound to the PNOM-cells within said cell population.

In another aspect of the invention, there is provided a method of detecting a PNOM-cell within a cell population, said method comprising: (i). contacting the cell population with compound represented by the structure set forth in any one of formulae I, II, III, IV, V, VI, VII, VIII, IX, X, XI, XII or XIII, or pharmaceutically acceptable salts, metal chelates, solvates and hydrates of the compound represented by the structure as set forth in any one formulae I, II, III, IV, V, VI, VII, VIII, IX, X, XI, XII or XIII, and solvates and hydrates of said salts; and (ii). determining the amount of said compound bound to said cells, wherein a significant amount of said compound bound to a cell indicates that the cell is being a PNOM-cell.

In another aspect of the invention, there is provided a method for detecting of PNOM-cells in a patient or an animal, the method comprising: (i). administering to the patient or animal a compound represented by the structure set forth in formulae I, II, III, IV, V, VI, VII, VIII, IX, X, XI, XII or XIII, or pharmaceutically acceptable salts, metal chelates, solvates and hydrates of the compound represented by the structure as set forth in formulae I, II, III, IV, V VI, VII, VIII, IX, X, XI, XII or XIII, and solvates and hydrates of said salts; and (ii) imaging the examined patient or animal, so as determine the amount of the compound bound to cells, wherein a significant amount of compound bound a cell indicates that the cell is being a PNOM-cell.

In another aspect of the invention, there is provided a pharmaceutical composition for targeting of drugs to foci of apoptosis or foci of activated platelets on blood clotting in a patient, where said patient is a human or non-human mammal, said pharmaceutical composition comprising a compound according to the structure set forth in formulae I, II, III, IV, V, VI, VII, VIII, IX, X, XI, XII or XIII, wherein said compound comprises or is being linked to a drug.

In another embodiment the invention provides a method of detecting a PNOM-cell in the brain of an examined subject, said method comprising: (i) administering a compound or a conjugate to the examined subject comprising said compound wherein said compound is represented by the structure set forth in formula (I):

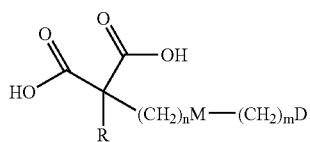

(I)

or pharmaceutically acceptable salts, metal chelates, solvates and hydrates of the compound represented by the structure as set forth in formula (I), and solvates and hydrates of said salts; wherein, R represents hydrogen, $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$ linear or branched alkyl, linear or branched hydroxy-alkyl, linear or branched fluoro-alkyl, one or two-ring aryl or heteroaryl, or combinations thereof; n and m each stands for an integer of 0, 1, 2, 3 or 4; n and m can be the same or different; M is selected from null, —O—, —S—, —C(O)NH—, and —N(U), wherein U stands for a null, hydrogen, $C_1$, $C_2$, $C_3$, or $C_4$ alkyl, D is a marker for diagnostics selected from a marker for imaging or a labeled metal chelate; said marker for imaging being selected from the group comprising a fluorescent label, a radio-label, a marker for X-ray, a marker for MRI, a marker for PET scan and a label capable of undergoing an enzymatic reaction that produces a detectable color; and where the above alkylene groups in formula (I) bound to M or D may be each substituted at each occurrence by a group selected from amino, F, OH and SH; and (ii) determining the amount of said compound bound to cells in the brain, wherein a significant amount of said compound bound to a cell indicates its being a PNOM-cell.

In another embodiment the invention provides a method of detecting a PNOM-cell in the brain of an examined subject, said method comprising: (i) administering a to the examined subject comprising a compound according to the structure set forth in formulae I, II, III, IV, V, VI, VII, VIII, IX, X, XI, XII or XIII, wherein said compound comprises or is linked to a marker for imaging or a labeled metal chelate; and (ii) determining the amount of said compound bound to cells in the brain, wherein a significant amount of said compound bound to a cell indicates its being a PNOM-cell.

In another embodiment, the invention provides a method of detecting cells undergoing a death process within a tumor in an examined subject, said method comprising:(i) administering to the examined subject a compound or a conjugate comprising said compound wherein the compound is represented by the structure set forth in formula (I):

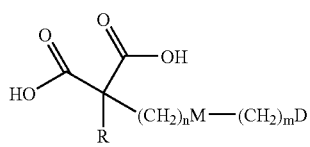

(I)

or pharmaceutically acceptable salts, metal chelates, solvates and hydrates of the compound represented by the structure as set forth in formula (I), and solvates and hydrates of said salts; wherein, R represents hydrogen, $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$ linear or branched alkyl, linear or branched hydroxy-alkyl, linear or branched fluoro-alkyl, one or two-ring aryl or heteroaryl, or combinations thereof; n and m each stands for an integer of 0, 1, 2, 3 or 4; n and m can be the same or different; M is selected from null, —O—, —S—, —C(O)NH—, and —N(U), wherein U stands for a null, hydrogen, $C_1$, $C_2$, $C_3$, or $C_4$ alkyl; D is a marker for diagnostics selected from a marker for imaging or a labeled metal chelate; said marker for imaging being selected from the group comprising a fluorescent label, a radio-label, a marker for X-ray, a marker for MRI, a marker for PET scan and a label capable of undergoing an enzymatic reaction that produces a detectable color; and where the above alkylene groups in formula (I) bound to M or D may be each substituted at each occurrence by a group selected from amino, F, OH and SH; and (ii) determining the amount of said compound bound to the examined tumor of said patient, wherein detection of a significant amount of said compound bound to cells in the tumor indicates that these tumor cells are undergoing a death process.

In another embodiment, the invention provides a method of detecting cells undergoing a death process within a tumor in an examined subject, said method comprising:(i) administering a to the examined subject compound according to the structure set forth in formulae I, II, III, IV, V, VI, VII, VIII, IX, X, XI, XII or XIII, wherein said compound comprises or is linked to a marker for imaging or a labeled metal chelate; and (ii) determining the amount of said compound bound to cells within the tumor, wherein detection of a significant amount of said compound bound to cells in the tumor indicates that these tumor cells are undergoing a death process.

In another embodiment, there is provided a method of targeting anticancer drugs to a tumor which has foci of apoptotic cells, said method comprising the step of administering a compound as set forth in any of the formulae I, II, III, IV, V, VI, VII, VIII, IX, X, XI, XII, and XIII which either comprises a cytotoxic drug or is being linked to a cytotoxic drug, thereby achieving targeting of said drugs to the foci of cell death within the tumor.

In another embodiment, there is provided a method of targeting an anticoagulant or a fibrinolytic agent to a blood clot, comprising the step of administering a compound as set forth in any of the formulae I, II, III, IV, V, VI, VII, VIII, IX, X, XI, XII, and XIII which either comprises said anticoagulant or fibrinolytic agent, thereby achieving targeting of said drugs to a blood clot.

BRIEF DESCRIPTION OF THE DRAWINGS

FIG. 2 a table which demonstrates the detection of cell death following middle cerebral artery (MCA) occlusion by tritium-labeled NST200.

DETAILED EMBODIMENTS OF THE INVENTION

Figure 1:
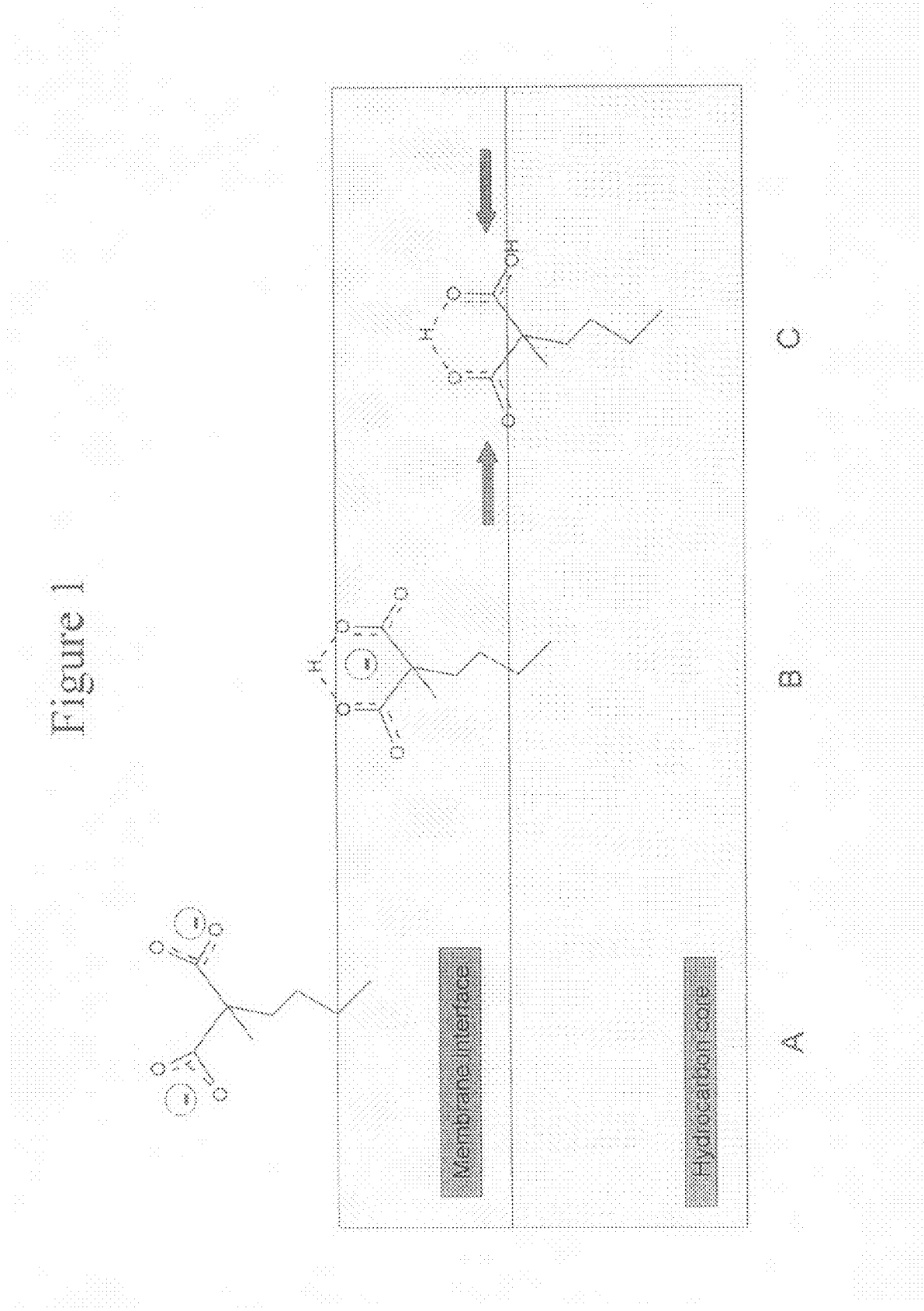
FIG. 1 demonstrates a scheme of the mechanism of action of the compounds of the invention: the NST-ML-Action Motif.

The present invention is related to compounds, capable of performing selective binding to cells undergoing perturbation of their normal organization of their plasma membrane (PNOM-cells), while binding to a lesser degree to cells maintaining the normal organization of their plasma membrane. The PNOM-cells are selected from cells undergoing a death process, apoptotic cells and activated platelets. The invention further relates to methods of detecting PNOM-cells by using compounds, which selectively bind to the PNOM-cells.

The compounds of the invention have the advantage of being active in performing selective targeting of PNOM-cells, while also featuring a relatively low molecular weight, and a potentially favorable pharmacokinetic profile.

In one embodiment of the invention, there is provided a compound which selectively targets to a PNOM cell (i.e., a PMBC) having the structure set forth in formula (I):

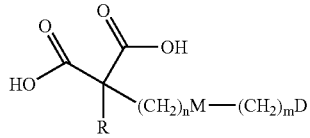

(I)

or pharmaceutically acceptable salts, metal chelates, solvates and hydrates of the compound represented by the structure as set forth in formula (I), and solvates and hydrates of said salts; wherein, R represents hydrogen, $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$ linear or branched alkyl, linear or branched hydroxy-alkyl, linear or branched fluoro-alkyl, one or two-ring aryl or heteroaryl, or combinations thereof; n and m each stands for an integer of 0, 1, 2, 3 or 4, n and m can be the same or different; M is selected from null, —O—, —S—, —C(O)NH—, and —N(U)—, wherein U stands for a null, hydrogen, $C_1$, $C_2$, $C_3$, or $C_4$ alkyl, or $C_1$, $C_2$, $C_3$, or $C_4$ alkylene; D is selected from hydrogen, a drug to be targeted to the PNOM-cell and a marker for diagnostics selected from a marker for imaging and a metal chelate; the marker for imaging may be detected by color, fluorescence, x-ray, CT scan, magnetic resonance imaging (MRI) or radio-isotope scan such as single photon emission tomography (SPECT) or positron emission tomography (PET); wherein the above alkylene groups bound to M or D, or the aryl or heteroaryl of R may each be substituted at each occurrence by a group selected from amino, F, $NO_2$, OH and SH.

The drug may be a medicinally-useful agent for the prevention, amelioration, or treatment of a specific disease and may be, for example, without being limited: an inhibitor of apoptosis, (e.g., a caspase inhibitor, antioxidant, modulator of the Bcl-2 system); an activator of cell death (e.g. an anticancer drug); or a modulator of blood coagulation, which may be an anticoagulant, an antithrombotic, or a thrombolytic agent. In such case, said drug is preferably selected among an anti-platelet agent, heparin, low molecular weight heparin, antagonists of glycoprotein IIb/IIIa, tissue plasminogen activator (tPA), or an inhibitor of a clotting factor, such as an inhibitor of thrombin or an inhibitor of factor Xa; or an anti-inflammatory drug or an immuno-modulatory drug. In an embodiment of the invention there is provided a method of targeting the drug to the area of interest such as an apoptotic foci in tumor so as to achieve amelioration or killing of the tumorogenic cells. In another embodiment of the invention, there is provided a method of treating a thrombosis by targeting anticoagulants to the thrombotic area so as to prevent, reduce or cease coagulation.

In another embodiment of the invention, D may be a solid support.

In another embodiment of the invention there is provided a compound which selectively targets a PNOM cell represented by the structure as set forth in formula (II):

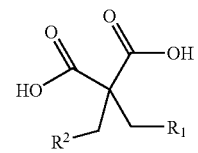

II including pharmaceutically acceptable salts hydrates, solvates and metal chelates of the compound represented by the structure as set forth in formula (II) and solvates and hydrates of said salts; wherein $R^1$ is hydrogen or $C_1$, $C_2$, $C_3$, $C_4$, $C_5$ or $C_6$ linear or branched alkyl, and $R^2$ is hydrogen or $C_1$, $C_2$, $C_3$, $C_4$, or $C_5$ or $C_6$ linear or branched alkyl, hydroxy-alkyl or fluoro-alkyl.

In another embodiment of the invention, there is provided a compound represented by the structure as set forth in formula (II) including pharmaceutically acceptable salts hydrates, solvates and metal chelates of the compound represented by the structure as set forth in formula (II) and solvates and hydrates of said salts; wherein $R^1$ is hydrogen or $C_1$, $C_2$, $C_3$, $C_4$, or $C_5$ linear or branched alkyl, and $R^2$ is $C_1$, $C_2$, $C_3$, $C_4$, or $C_5$ fluoro-alkyl.

In another embodiment of the invention there is provided a compound represented by the structure as set forth in formula (III):

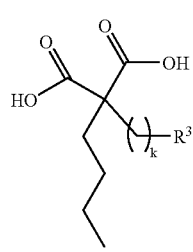

III including pharmaceutically acceptable salts hydrates, solvates and metal chelates of the compound represented by the structure as set forth in formula (II) and solvates and hydrates of said salts; wherein $R^3$ is hydroxyl or F and k is an integer selected from 1, 2, 3, 4 and 5.

In another embodiment of the invention there is provided a compound represented by the structure as set forth in formula (IV):

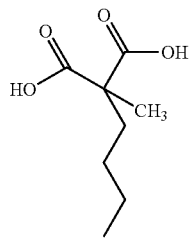

IV including pharmaceutically acceptable salts hydrates, solvates and metal chelates of the compound represented by the structure as set forth in formula (IV) and solvates and hydrates of said salts; said compound is designated NST200.

In another embodiment of the invention there is provided a compound represented by the structure as set forth in formula (V):

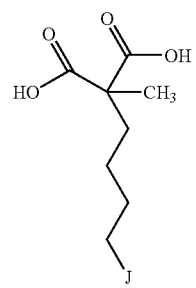

V including pharmaceutically acceptable salts hydrates, solvates and metal chelates of the compound represented by the structure as set forth in formula (V) and solvates and hydrates of said salts; wherein J is selected from —F and —OH. In the case that J is —F, said compound is designated NST201.

In yet another embodiment of the invention there is provided a compound represented by the structure as set forth in formula (VI):

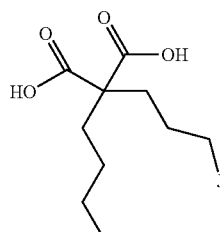

VI including pharmaceutically acceptable salts hydrates, solvates and metal chelates of the compound represented by the structure as set forth in formula (VI) and solvates and hydrates of said salts; wherein J is selected from hydrogen, —F and —OH. In the case that J is —F, said compound is designated NST204.

In another embodiment of the invention there is provided a compound represented by the structure set forth in formula VII:

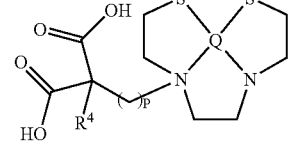

VII including pharmaceutically acceptable salts hydrates, solvates and metal chelates of the compound represented by the structure as set forth in formula (VII) and solvates and hydrates of said salts, wherein Q is selected from Technetium, oxo-Technetium, Rhenium and oxo-Rhenium, $R^4$ is selected from hydrogen, $C_1$, $C_2$, $C_3$, $C_4$, $C_5$, and $C_6$ linear or branched alkyl, and p stands for an integer, selected from 1, 2, 3, 4 and 5.

In another embodiment of the invention there is provided a compound represented by the structure set forth in formula VIII:

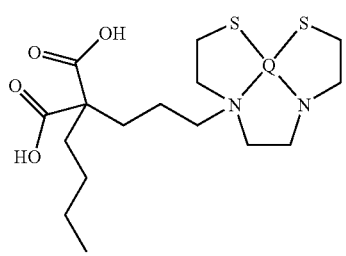

VIII including pharmaceutically acceptable salts hydrates, solvates and metal chelates of the compound represented by the structure as set forth in formula (VIII) and solvates and hydrates of said salts, wherein Q is selected from Technetium, oxo-Technetium, Rhenium and oxo-Rhenium.

In another embodiment of the invention there is provided a compound represented by the structure set forth in formula IX:

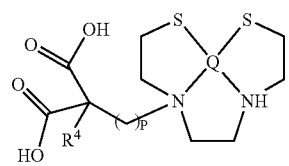

IX including pharmaceutically acceptable salts hydrates, solvates and metal chelates of the compound represented by the structure as set forth in formula (IX) and solvates and hydrates of said salts, wherein Q is selected from Technetium, oxo-Technetium, Rhenium and oxo-Rhenium, $R^4$ is selected from hydrogen, $C_1$, $C_2$, $C_3$, $C_4$, $C_5$, and $C_6$ linear or branched alkyl, and p stands for an integer, selected from 1, 2, 3, 4 and 5. In another embodiment of the invention there is provided a compound represented by the structure as set forth in formula (X):

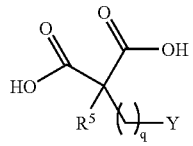

X including pharmaceutically acceptable salts hydrates, solvates and metal chelates of the compound represented by the structure as set forth in formula (X) and solvates and hydrates of said salts; wherein $R^5$ is selected from hydrogen, $C_1$, $C_2$, $C_3$, $C_4$, $C_5$, and $C_6$ linear or branched alkyl, $C_1$, $C_2$, $C_3$, $C_4$, $C_5$, and $C_6$ linear or branched fluoro-alkyl, and $C_1$, $C_2$, $C_3$, $C_4$, $C_5$, and $C_6$ linear or branched hydroxy-alkyl; q stands for an integer, selected from 1, 2, 3, 4 and 5; and Y is a marker for fluorescence. In an embodiment of the invention, Y is selected from a dansyl-amide group and fluorescein.

In another embodiment of the invention there is provided a compound represented by the structure as set forth in formula (XI):

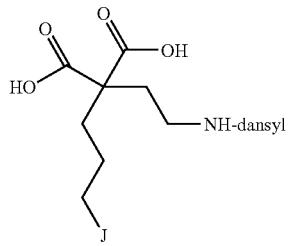

XI including pharmaceutically acceptable salts hydrates, solvates and metal chelates of the compound represented by the structure as set forth in formula (XI) and solvates and hydrates of said salts; wherein J is selected from hydrogen, methyl, —F and —OH. In the case that J is methyl, the compound is designated NST203.

In another embodiment of the invention there is provided a compound represented by the structure as set forth in formula (XII):

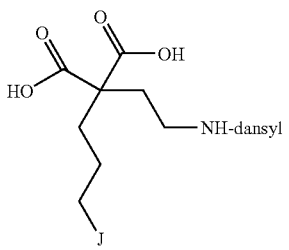

XII including pharmaceutically acceptable salts hydrates, solvates and metal chelates of the compound represented by the structure as set forth in formula (XII) and solvates and hydrates of said salts; wherein J is selected from hydrogen, methyl, —F and —OH.

In another embodiment of the invention there is provided a compound represented by the structure as set forth in formula (XIII):

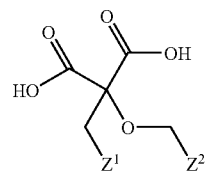

XIII including pharmaceutically acceptable salts hydrates, solvates and metal chelates of the compound represented by the structure as set forth in formula (XIII) and solvates and hydrates of said salts; wherein $Z^1$ and $Z^2$ are each selected from hydrogen and $C_1$, $C_2$, $C_3$, $C_4$, $C_5$ alkyl, hydroxy-alkyl or fluoro-alkyl; Z groups may be the same or different.

In another embodiment of the invention each of the compounds represented by formulae I, II, III, IV, V, VI, VII, VIII, IX, X, XI, XII or XIII, may comprise or may be linked to a marker for diagnostics such as for example without being limited Tc, Tc=O, In, Cu, Ga, Xe, Tl, Re and Re=O, $^{123}$I, $^{131}$I, Gd(III), Fe(III), $Fe_2O_3$, $Fe_3O_4$, Mn(II) $^{18}$F, $^{15}$O, $^{18}$O, $^{11}$C, $^{13}$C, 124I, $^{13}$N, $^{75}$Br, Tc-99m or In-111.

In another aspect of the invention, there is provided a method of detecting a PNOM-cell within a cell population, said method comprising: contacting the cell population with a compound represented by any one of the structure set forth in formulae I, II, III, IV, V, VI, VII, VIII, IX, X, XI, XII or XIII, or pharmaceutically acceptable salts, metal chelates, solvates and hydrates of the compound represented by the structure as set forth in formulae I, II, III, IV, V, VI, VII, VIII, IX, X, XI, XII or XIII, and solvates and hydrates of said salts; and determining the amount of the compound bound to said cells, wherein a significant amount of compound bound to a cell indicates its being a PNOM-cell.

The term "significant amount of the compound bound to a cell" refers according to the invention to the amount of the compound of the invention, comprising or is being attached to a marker for diagnostics, which binds to a PNOM-cell in an amount which is at least 30% greater than the amount bound to a normal cell. In another embodiment, the amount may be higher by 50%. In another embodiment of the invention, the amount may be higher by 75%. In another embodiment, the amount may be higher by 150%. In another embodiment the amount may be higher by about two fold. In another embodiment the amount may be higher than at least two fold. In another embodiment, the amount may be higher than at least five fold. In another embodiment, the amount may be higher by at least ten fold.

In an embodiment of the invention, relating to use of the compounds of the invention for obtaining images of cells undergoing a death process in a patient via radio-nuclide imaging by PET or SPECT, the calculation of the ratio between the amount of the compound bound to the PNOM-cells vs. the amount bound to the normal cells may be conducted by comparing the amplitude or intensity of the signal obtained from the tissue inflicted by the death process, with the amplitude/intensity obtained from an organ not-inflicted by said process.

According to another aspect of the invention, there is provided a method for detecting of PNOM-cells in a patient or an animal, the method comprising: administering a compound to the patient or animal a compound represented by the structure set forth in formulae I, II, III, IV, V, VI, VII, VIII, IX, X, XI, XII or XIII, wherein said compound comprises a marker for imaging, or pharmaceutically acceptable salts, metal chelates, solvates and hydrates of the compound represented by the structure as set forth in formulae I, II, III, IV, V, VI, VII, VIII, IX, X, XI, XII or XIII, and solvates and hydrates of said salts; and (ii) imaging the examined patient or animal, so as determine the amount of compound bound to cells, wherein detection of a significant amount of compound bound to cells indicates that these cells are PNOM-cells.

The mechanism of action of the compounds of the invention comprises, at least in part, the activity of a module shared by all the compounds, having the general formula XIII, and designated NST-ML-Action Motif:

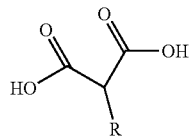

wherein R stands for a $C_1$, $C_2$, $C_3$, $C_4$, or $C_5$ alkyl. In an embodiment of the invention, R is butyl.

The NST-ML-Action Motif is designed to correspond to the structural alterations encountered in the plasma membranes of apoptotic cells, which distinguish said membranes from membranes of healthy cells. This complex of membrane alterations comprises:

(i). Scrambling of membrane phospholipids, with exposure on the cell surface of phosphatidylethanolamine (PE) and the negatively-charged phosphatidylserine (PS).

Exposure of PS on the cell surface leads to a negative surface electric potential, and attraction of protons form the bulk to the membrane interface.

(ii). The increase in the fraction of aminophospholipids (PE and PS) within the outer leaflet of the membrane results in an enhancement of the proton currents in the interface of the outer leaflet of the membrane (interfacial proton currents, IPC). This enhancement is due to the substantial increase in the number of functionalities amenable to participation in proton transfer reactions, as PE and PS replace phosphatidylcholine (PC) and sphingomeylin (SM) in the outer membrane leaflet. PE comprises a primary amine, while PS comprises a primary amine and a carboxyl group. By contrast, PC and SM comprise each a quaternary ammonium, that bears a permanent positive charge, and thus cannot participate in proton transfer reactions.

(iii). In addition, apoptotic membranes are characterized by a reduced level of packing of the membrane constituents.

In a non limiting hypothesis of the mode of action of the NST-ML-Action Motif, it comprises a switch moeity, activated selectively upon its approaching a membrane which features the above characteristics, i.e., the plasma membrane of an apoptotic cell (FIG. 1). The Action Motif is highly soluble in aqueous solution, due to its having two negatively-charged carboxyl groups (pKa of alkylmalonate is about 5.6 and 2.8), thus having a formal charge of −2 in physiological conditions. However, upon approaching the apoptotic membrane, due to the more acidic surface, and due to the reduction in the dielectric constant of the interfacial environment, which acts to elevate pKa values of the carboxyl groups, a proton is being captured by the malonate moeity.

The capture of the proton by the malonate group neutralizes one of the negative charges, and renders the overall charge of the molecule to −1. Moreover, the capture of the proton further leads to a very unique situation, which includes the following:

(i). An acid-anion pair is formed, wherein an exceptionally strong hydrogen bond is formed between the protonated and unprotonated carxoyl groups. This hydrogen bond is strong, symmetrical and stabilized by resonance and tautamerization.

(ii). This leads to distribution of the negative charge over the four carboxyl atoms, i.e., its being partially delocalized.

(iii). The strong acid-anion hydrogen bond rigidifies the molecule, creating a bulky, rigid, flat, six-membered ring, bearing a partially-delocalized negative charge, and comprising pi-electron clouds over the carboxyl bouble bonds. Such an element undergoes according to a non-limiting hypothesis of the mechanism of action of the compounds of the invention a relatively favorable penetration into the membrane interface. However, its bulky, rigid structure directs its binding selectively to loosely packed membranes, i.e., apoptotic membranes, rather than binding to highly-packed membranes such as the plasma membranes of healthy cells. These steric features therefore promote selectivity in binding to the apoptotic membranes.

Upon the selective penetration of the single-protonated malonate into the membrane interface, it becomes subject to the enhanced interfacial proton currents, and becomes integrated within an extensive interfacial network of hydrogen bonds. The probability for a second proton to be acquired by the malonate moeity under these conditions is markedly increased. This will further lead to neutralization of charge and formation of further acid-anion pairs with adjacent phospholipid molecules. Taken together, these events will act to stabilize the binding of the molecule to the interface of the apoptotic membrane.

The penetration of the protonated malonate moiety into the membrane interface and the stabilization of its binding there allow the alkyl chain R to traverse the membrane interface, to reach its optimal binding environment, i.e., the membrane hydrocarbon core, and to contribute through hydorphobic interactions to the free energy gain of compound binding The NST-ML-Action Motif is being utilized for useful diagnostic or therapeutic purposes, through its binding to a marker for imaging or a therapeutic drug (moiety D in Formula I) through a hydrocarbon linker [$(CH_2)_m$ of Formula I]. The NST-ML-Action Motif according to this approach acts as a targeting moeity, allowing selective targeting of the marker for imaging, or the drug attached to it to cells and tissues inflicted by cell death, paricularly apoptosis, or tissues inflicted by platelet activation and thrombosis.

FIG. 1 demonstrates NST200 (Formula IV), and describes the three stages of its approach and binding to the PNOM membrane in physiological conditions:

A: The compound is in aqueous solution, thus both carboxyl groups are deprotonated, i.e., negatively charged, and the compound is highly soluble.

B: Upon approaching the negatively charged apoptotic membrane, the compound acquires a proton. An anion-acid dimer is formed, thus creating a stable six-membered, resonance-stabilized ring, which penetrates the membrane interface. The bulky, rigid ring structure assists in selectivity, since its steric features favor binding to the more loosely packed plasma membrane of the apoptotic cell.

C: Upon compound penetration into the membrane interface, it is subjected to the interfacial network of hydrogen bonds, and to the augmented interfacial proton currents encountered in the interface of the apoptotic membrane. The resultant protonation and hydrogen bonding further acts to stabilize the binding of the compound to the interface (arrows). The alkyl chain further contributes to the free energy gain of binding through formation of hydrophobic interactions with the membrane hydrocarbon core.

The compounds of the invention may be used for selective targeting of medicinally-useful agents to tissues and organs comprising PNOM-cells, in three different approaches of the invention:

(i). According to a first approach, termed hereinafter the "detection approach" said selective binding may be utilized to targeting a marker for imaging to PNOM-cells. This may be used in clinical practice, either in vivo, ex vivo or in vitro, for the diagnosis of diseases in which such cells emerge as will be explained herein below.

(ii). According to a second approach, termed hereinafter the "therapeutic approach", said property of selective binding is used for selective targeting of therapeutic agents to organs and tissues in the body wherein PNOM-cells emerge, e.g., regions of cell death, thrombus formation or inflammation.

(iii). In accordance with a third approach of the invention termed the "clearance approach", the selective binding of the compounds of the invention to PNOM-cells is utilized, via attachment of said compounds to a solid support, to clear body fluids such as blood from PNOM-cells, which may be potentially hazardous due to their pro-coagulant properties.

In accordance with the detection approach, the present invention concerns a composition comprising as an effective ingredient a PMBC, comprising or linked to a marker for imaging, for the detection of PNOM-cells, either in vitro, ex vivo or in vivo. Such a PMBC is hereinafter designated "diagnostic PMBC". The diagnostic PMBC is capable of performing selective binding to PNOM-cells present in the assayed sample. Then, said binding may be identified by any means known in the art. The diagnostic PMBC of the invention enables the targeting of said marker, by the PMBC, to PNOM-cells in a selective manner. Then, the detectable label can be detected by any manner known in the art, and in accordance with the specific label used, for example, fluorescence, radioactive emission, or a color production, MRI, x-ray and the like. In one embodiment, the diagnostic PMBC is linked to the detectable label by a covalent or a non-covalent (e.g., electrostatic) binding.

In one embodiment, the detectable label may be any of the respective radioisotopes of the metal ions Tc, oxo-Tc, In, Cu, Ga, Xe, Tl and Re, oxo-Re and the covalently linked atoms: $^{123}I$ and $^{131}I$ for radio-isotope scan such as SPECT, Gd(III), Fe(III) or Mn(II) for MRI, and $^{18}F$, $^{15}O$, $^{18}O$, $^{11}C$, $^{13}C$, $^{124}I$, $^{13}N$ and $^{75}Br$ for positron emission tomography (PET) scan.

In an embodiment, the PMBC of the invention is aimed at clinical imaging of apoptosis via PET scan, and the PMBC comprises $^{18}F$ atom(s).

The attachment of $^{18}F$ for the purposes of clinical PET imaging may be performed immediately before the administration of the diagnostic compound to the patient. Therefore, it may be useful to synthesize a PMBC-PET precursor, comprising a moiety to be substituted by $^{18}F$ before administration to the patient. In one embodiment, said moiety to be replaced by $^{18}F$ is selected from a hydroxyl group, a nitro group, or a halogen atom such as bromine or chlorine. Such a PMBC-PET precursor is also included in the scope of the invention.

The method for labeling a PMBC, which can be any PMBC of the structures described above, with $^{18}F$ for PET imaging, comprises the step of attaching an $^{18}F$ atom to the PMBC; thereby radio-labeling a PMBC with $^{18}F$ for PET imaging. Optionally, the functional groups of the PMBC may be protected by appropriate protecting groups prior to the step of attaching $^{18}F$ atom, and are removed after the step of attachment of the $^{18}F$ atom.

In the case that the marker is a metal atom (e.g., Gd, $^{99m}Tc$ or oxo-$^{99m}Tc$ for MRI or SPECT, respectively), the PMBC comprises a metal chelator. The metal coordinating atoms of said chelator may be nitrogen, sulfur or oxygen atoms. In another embodiment of the invention, said chelator is diaminedithiol, monoamine-monoamide-bisthiol (MAMA), triamide-monothiol, and monoamine-diamide-monothiol. In such case, both a PMBC-chelate precursor, being the PMBC attached to or comprising a chelator prior to complexation with the metal atom, and the complex comprising the metal atom, are included in the scope of the invention.

For fluorescent detection, the diagnostic PMBC may comprise a fluorescent group selected among any fluorescent probe known in the art. Examples for said probes are 5-(dimethylamino) naphthalene-1-sulfonylamide (dansyl-amide), and fluorescein.

The compounds of the invention may be used for a detection and diagnosis of a wide variety of medical conditions such as which are characterized by formation PNOM-cells. Examples of clinical conditions characterized by PNOM-cells are as follows:

Diseases which are characterized by occurrence of excessive apoptosis, such as degenerative disorders, neurodegenerative disorders (e.g., Parkinson's disease, Alzheimer's disease, Huntington chorea), AIDS, ALS, Prion Diseases, myelodysplastic syndromes, ischemic or toxic insults, graft cell loss during transplant rejection; tumors, and especially highly malignant/aggressive tumors, are also often characterized by enhanced apoptosis, in addition to the excessive tissue proliferation. The tumors may be tumors derived, without being limited from the lung, breast or colon.

Example 3 of the invention as well as FIG. 2, exemplify the performance of a compound of the invention to detect brain cells undergoing a death process. The trigger for the cell death was ischemia/reperfusion. The damaged brain hemisphere manifested two-fold higher levels of uptake of tritium-labeled NST200, compared with the contralateral non-damaged hemisphere.

Diseases manifested by excessive blood clotting, wherein PNOM occurs during platelet activation, and/or during activation of or damage to other cellular elements (e.g., endothelial cells). These diseases include, among others, arterial or venous thrombosis, thrombo-embolism, e.g., myocardial infarction, cerebral stroke, deep vein thrombosis, disseminated intravascular coagulation (DIC), thrombotic thrombocytopenic purpura (TTP), sickle cell diseases, thalassemia, antiphospholipid antibody syndrome, systemic lupus erythematosus.

Inflammatory disorders, and/or diseases associated with immune-mediated etiology or pathogenesis, auto-immune disorders such as antiphospholipid antibody syndrome, systemic lupus erythematosus, connective tissue disorders such as rheumatoid arthritis, scleroderma; thyroiditis; dermatological disorders such as pemphigus or erythema nodosum; autoimmune hematological disorders; autoimmune neurological disorders such as myasthenia gravis; multiple sclerosis; inflammatory bowel disorders such as ulcerative colitis; vasculitis.

Atherosclerotic plaques, and especially plaques that are unstable, vulnerable and prone to rupture, are also characterized by PNOM-cells, such as apoptotic macrophages, apoptotic smooth muscle cells, apoptotic endothelial cells, and activated platelets.

Said detection may also be carried out in a person already known to have the disease for the purpose of evaluating the disease severity and in order to monitor disease course and/or response to various therapeutic modalities. A non-limited example for such monitoring is evaluation of response to anticancer therapy. Since most anti-tumor treatments, such as chemotherapy or radiotherapy exert their effect by induction of apoptosis, detection by a diagnostic PMBC of therapy-induced apoptosis of tumor cells may teach on the extent of sensitivity of a tumor to the anti-tumor agent. This may substantially shorten the lag period between the time of administration of the anti-cancer treatment and the time of proper assessment of its efficacy.

Moreover, said detection may be also used to monitor adverse effects of anti-cancer treatments. A large part of such adverse effects is due to untoward treatment-induced apoptosis in normal, yet sensitive cells, such as those of the gastrointestinal epithelium or the bone marrow hematopoietic system.

In addition, said detection may aim at characterization of intrinsic apoptotic load within a tumor, often correlated with the level of tumor aggressiveness; and may also assist in the detection of metastases, via detection of the intrinsic apoptosis frequently occurring within metastases.

Similarly, the diagnostic PMBC of the invention may be useful in monitoring graft survival after organ transplantation, since apoptosis plays a major role in cell loss during graft rejection.

In addition, said detection may aim at monitoring response to cyto-protective treatments, and thus aid in screening and development of drugs which are capable of inhibiting cell loss in various diseases (for example those recited above) by enabling a measure of assessment of cell death.

Said detection may be also useful for the detection of atherosclerotic plaques, since destabilization of such plaques, rendering them vulnerable, prone to rupture, thrombosis and embolization, is characterized by participation of several types of PNOM-cells, including apoptotic cells (apoptotic macrophages, smooth muscle cells and endothelial cells), and activated platelets.

In accordance with this approach, the present invention is related to a method of detection of PNOM-cells in a cell population, selected from whole body, organ, tissue, tissue culture or any other cell population, said method comprising: (i). contacting the cell population with a PMBC according to any of the embodiments of the invention; and (ii). determining the amount of PMBC bound to said cell population, wherein detection of a significant amount of compound bound to a cell within said population indicates that the cell is a PNOM-cell.

Examples 4 and 6 which show the ability of tritium labled NST 200 and NST 203 to bind to apoptotic cells in higher amount than to non apoptotic cells, demonstrate that the compounds of the invention have the property of selective binding and detecting apoptotic cells.

In another embodiment, the present invention further relates to a method for detecting PNOM-cells in a patient or in an animal in vivo, the method comprising: (i). administering a diagnostic PMBC to the examined patient or animal; said administration being performed by any means known in the art, such as parenteral (e.g., intravenous) or oral administration; and (ii). imaging the examined patient or animal, by any method known in of the art (e.g., PET scan, SPECT, MRI), to detect and determine the amount of diagnostic PMBC bound to cells, wherein a significant amount of compound bound to a cell indicates that the cell is a PNOM-cell.

In another embodiment of the invention, the present invention is related to a method for the detection of PNOM-cells in a tissue or cell culture sample in vitro or ex-vivo, the method comprising: (i). contacting said sample with a diagnostic PMBC, which may be any of the PMBC compounds described in the invention under conditions enabling binding of said diagnostic PMBC to biological membranes of PNOM-cells; and (ii). detecting the amount of diagnostic PMBC bound to said cells; the presence of a significant amount of bound diagnostic compound indicating the presence of PNOM-cells within said tissue or cell culture.

The step of detection in said in vitro or ex-vivo studies may be for example, in the case of fluorescent-labeled compound of the invention, without limitation by using flow cytometric analysis, which permits cell visualization on equipment that is widely commercially available. In an example using fluorescence to visualize cells, a single 15 mW argon ion laser beam (488 nm) is used to excite the FITC fluorescence, and fluorescence data is collected using 530 nm band pass filter to provide a histogram. The percent of fluorescent cells can be calculated, for example using Lysis II software or any other software. The method for detection may be used in an embodiment of the invention for screening therapeutic drugs such as anticancer drugs.

The term "significant amount" according to the invention means that the amount of PMBC bound to a PNOM-cell is at least 30% higher than the amount bound to a non-PNOM-cell. The actual amount may vary according to the imaging method and equipment utilized, and according to the organs or tissues examined. In another embodiment the amount of PMBC bound to a PNOM-cell is at least 50% higher than the amount bound to a non-PNOM-cell. In another embodiment the amount of PMBC bound to a PNOM-cell is at least 75% higher than the amount bound to a non-PNOM-cell. In another embodiment the amount of PMBC bound to a PNOM-cell is at least twice times the amount bound to a non-PNOM-cell. In another embodiment the amount of PMBC bound to a PNOM-cell is at least four times the amount bound to a non-PNOM-cell. In another embodiment the amount of PMBC bound to a PNOM-cell is at least six times the amount bound to a non-PM-cell. In another embodiment the amount of PMBC bound to a PNOM-cell is at least eight times the amount bound to a non-PNOM-cell. In another embodiment the amount of PMBC bound to a PNOM-cell is at least ten times the amount bound to a non-PNOM-cell.

The action of the binding depends inter-alia on the method of measuring said difference in binding. The method of the present invention may be used for the diagnosis of a disease characterized by the occurrence of PNOM-cells, for example, without being limited to any of the diseases mentioned above.

The method of the present invention may also be used for monitoring the effects of various therapeutic modalities for said diseases or medical conditions, or alternatively for basic science research purposes as explained above.

In accordance with a second approach of the invention, termed "the therapeutic approach", the present invention concerns a pharmaceutical composition comprising a PMBC which is used in targeting an active drug or a pro-drug to PNOM-cells. In an embodiment of the invention, the PMBC may comprise a drug or in another embodiment of the invention may be a conjugate which comprises PMBC and a medicinally-useful agent. By the term "conjugate" it is meant two molecules that are linked together by any means known in the art, such as covalent bonding.

The association between the medicinally-useful drug and the PMBC wherein it is comprised or linked to may be by covalent binding, by non-covalent binding (e.g., electrostatic forces) or by formation of carrier particles (such as liposomes) comprising the drug and having on their surface a PMBC which targets the complex to the PNOM-cells. Once the drug reaches the target, it should be able to exert its physiological activity, either when still being part of the PMBC-conjugate, after disconnecting from the PMBC unit (for example by cleavage, destruction, etc., activity of natural enzymes), by phagocytosis of drug-containing liposomes having PMBC on their membrane, or by any other known mechanism.

The drug should be chosen in accordance with the specific disease for which the composition is intended.

The pharmaceutical composition as well as the diagnostic composition of the invention may be administered by any of the known routes, inter alia, oral, intravenous, intraperitoneal, intramuscular, subcutaneous, sublingual, intraocular, intranasal or topical administration, or intracerebral administration. The carrier should be selected in accordance with the desired mode of administration, and include any known components, e.g. solvents; emulgators, excipients, talc; flavors; colors, etc. The pharmaceutical composition may comprise, if desired, also other pharmaceutically-active compounds which are used to treat the disease, eliminate side effects or augment the activity of the active component.

In accordance with this aspect, the present invention still further concerns a method for treating a disease manifesting PNOM-cells, comprising administering to an individual in need of such treatment an effective amount of a therapeutic PMBC, said therapeutic PMBC comprising a drug being active as a treatment for said disease or a pro-drug to be converted to an active drug in the targeted area. The therapeutic PMBC allows for selective targeting of the drug to the tissues comprising PNOM-cells, thus augmenting its local concentration, and potentially enhancing its therapeutic effect at the target site. Such medical disorders are those defined above.

In another embodiment, there is provided a method of killing cancer cells in a tumor comprising a foci of apoptotic cells comprising the step of targeting an apoptotic cell in a foci of apoptotic cells with any one of the compounds set forth in formulae I, II, III, IV, V, VI, VII, VIII, IX, X, XI, XII, and XIII which either comprise a cytotoxic drug or is linked to a cytotoxic drug thereby killing the cancer cells. In one embodiment, the method of killing cells involves an autocatalytic mechanism in which in the beginning the compound comprising a cytotoxic drug or a conjugate of a compound and a cytotoxic drug, is targeted to the apoptotic foci. Then, following the action of the cytotoxic drug, the foci is increased in its volume and accordingly more of the compound or the conjugate will be targeted to the apoptotic foci. Accordingly, the mechanism of action of the compound comprising the cytotoxic drug or a conjugate of a compound and a cytotoxic drug is augmented with the time.

The term "effective amount" refers to an amount capable of decreasing, to a measurable level, at least one adverse manifestation of the disease, and should be chosen in accordance with the drug used, the mode of administration, the age and weight of the patient, the severity of the disease, etc.

In another embodiment the compounds of the invention may comprise or may be linked to a radioisotope which has therapeutic effect. An Example without limitation is Yttrium 90 Iodine 131 Rhenium 188 Holmium 166 Indium 111 Lutetium 177 or any other radioisotopes emitting radiation useful for therapeutic purposes.

25. A method of reducing/preventing a blood clot comprising activated platelets, comprising the step of targeting the activated platelets in a blood clot with any one of the compounds set forth in formulae I, II, III, IV, V, VI, VII, VIII, IX, X, XI, XII, and XIII which either comprise an coagulant modulator or is linked to a coagulant modulator, thereby reducing/preventing the blood clot.

This method may be used also to treat or prevent diseases manifested by excessive blood clotting, wherein PNOM occurs during platelet activation, and/or during activation of or damage to other cellular elements (e.g., endothelial cells). These diseases include, among others, arterial or venous thrombosis, thrombo-embolism, e.g., myocardial infarction, cerebral stroke, deep vein thrombosis, disseminated intravascular coagulation (DIC), thrombotic thrombocytopenic purpura (TTP), sickle cell diseases, thalassemia, antiphospholipid antibody syndrome, systemic lupus erythematosus.

According to a third approach of the invention, termed the "clearance approach" the properties of the PMBCs of the invention to bind specifically to PNOM-cells are utilized to clear body fluid of said cells. In an embodiment of the invention, the body fluid is blood or a blood product.

Many surgical or medical interventions requiring extracorporeal circulation are associated with exposure of blood elements to exogenous artificial environment. This often leads to activation of and damage to blood cells, systemic inflammation, and thromboembolic phenomena, potentially having serious clinical consequences, such as neurological dysfunction upon lodging of microemboli in the cerebral blood vessels. It is therefore desirable to detect and remove said damaged, activated or apoptotic cells from blood.

Thus, according to one of its aspects, the present invention concerns a PMBC immobilized on a solid support. Said immobilization may be by direct attachment, either by covalent or non-covalent binding, or by attachment through a spacer. The immobilized PMBC is intended to clear a body fluid from PNOM-cells.

According to another embodiment of the present invention, the solid support features a plurality of beads to which the PMBC are bound. Preferably, the beads are resin-coated beads. Alternatively, the beads may be magnetic beads.

Where the solid support includes a plurality of fibers or micro-capillara, among and/or through which the body fluid flows, the inner and/or outer faces thereof are covered with the PMBC.

The compounds immobilized on a solid support form part of a filter device. Thus in accordance with the clearance approach, the present invention further concerns a filter device comprising a housing containing the PMBC immobilized on said solid support, and a fluid inlet and fluid outlet. Body fluids such as blood or blood products enter the housing through said inlet, come into contact and adhere to the immobilized PMBC contained in the housing. Thus, the body fluid is cleared of circulating cells having perturbed membranes, such as damaged or dying cells, or cleared of larger structures such as emboli having PNOM membranes. Consequently, fluid exiting from said outlet has a reduced content of said PNOM-cells or is essentially devoid of same.

The filter device may form a replaceable, a permanent, or an add-on portion of an extracorporeal circulation apparatus. Thus the present invention also concerns an extracorporeal circulation apparatus comprising said filter device, wherein blood circulating through the apparatus also passes through the device.

Examples of such apparatuses are a cardiopulmonary bypass apparatus; a hemodialysis apparatus; a plasmapheresis apparatus and a blood transfusion apparatus, such as state of the art blood transfusion bags.

EXAMPLES

In order to understand the invention and to see how it may be carried-out in practice, the following examples are described: examples directed to synthesis of the compounds of the invention; and examples directed to the performance of the compounds of the invention in selective binding to cells undergoing death process. In order to allow detection of the compounds of the invention, they were either radio-labeled with tritium. In some of the Examples, the compounds were labeled by attachment to a fluorescent label, i.e., a dansylamide group, thus allowing fluorescent microscopy. The selectivity of binding of the compounds to the apoptotic cells was demonstrated in vitro, in tissue cultures, and in vivo, in a murine model of cerebral stroke, wherein cell death was induced by occlusion of the middle cerebral artery, and in a murine model of melanoma.

Example I

Synthesis of NST-ML-F-4(2-butyl-2(3-fluoropropyl)-malonic acid); (Scheme 1)

Di-t-butyl malonate (5 mL) was deprotonated with 1 eq of NaH in dimethyl formamide (DMF), and 1 eq of n-butyl iodide was added after the hydrogen evolution ceased. The reaction mixture was heated to 50° C. for 14 hours. 5.8 g di-t-butyl, butyl malonate (2) were obtained in a 95% yield by using column chromatography. 2 (3.8 g) was treated with NaOCH$_3$ (0.05 eq, cat.) and acrolein (1.1 eq) in toluene to afford 1.26 g of aldehyde (3) in a 30% yield. Compound 3 was then reacted with NaBH$_4$ (1.05 eq) in a mixture of ether/water (8:1 v/v) for two hours. After work-up and flash chromatography, pure alcohol 4 was obtained (93%). The resulted product was treated with 1.1 eq of methansulfonyl chloride (MsCl) and 2.2 eq of triethyl amine (Et$_3$N) so as to obtain mesylate compound 5 in 97% yield. This product was essentially pure and directly carried over to the next reaction with no further purification.

A mixture of KF (5 eq), kryptofix (5 eq) and K$_2$CO$_3$ (2.5 eq) in 2 mL of acetonitrile was stripped to dryness under a stream of nitrogen for 4 times. The mesylate compound 5 (167 mg) in 2 mL of acetonitrile was then added. The reaction was stirred in a 120° C. sand bath for 10 min. Upon work-up, $^1$H NMR of the crude product showed a mixture of the desired product 6 and kryptofix.

Deprotection of the di-t-butyl ester 6 was performed with (474 mg) and trifluoroacetic acid (TFA) (17 mL) at 10° C. for 30 min, and then evaporated to dryness. The residual material was evaporated twice from chloroform and dried on the vacuum line to afford a white solid (312 mg, 99%) of NST-ML-F-4.

NMR data of the compound are: $^1$H NMR (300 MHz, CDCl$_3$) δ 4.41 (dt, $J_f$=5.9 Hz, $J_d$=47.4 Hz, 2H), 1.97-1.91 (m, 2H), 1.89-1.83 (m, 2H), 1.69-1.60 (m, 1H), 1.58-1.52 (m, 1H), 1.33 (p, J=6.9 Hz, 2H), 1.25-1.14 (m, 2H), 0.92 (t, J=7.2 Hz, 3H); $^{13}$C NMR (75 MHz, CD$_3$OD) δ 175.8, 86.2, 84.1, 58.6, 34.1, 30.1, 30.0, 27.9, 27.3, 27.0, 24.5, 14.6; $^{19}$F NMR (282 MHz, CD$_3$OD) δ −220.9; MS (EI) m/z 219 (M−H).

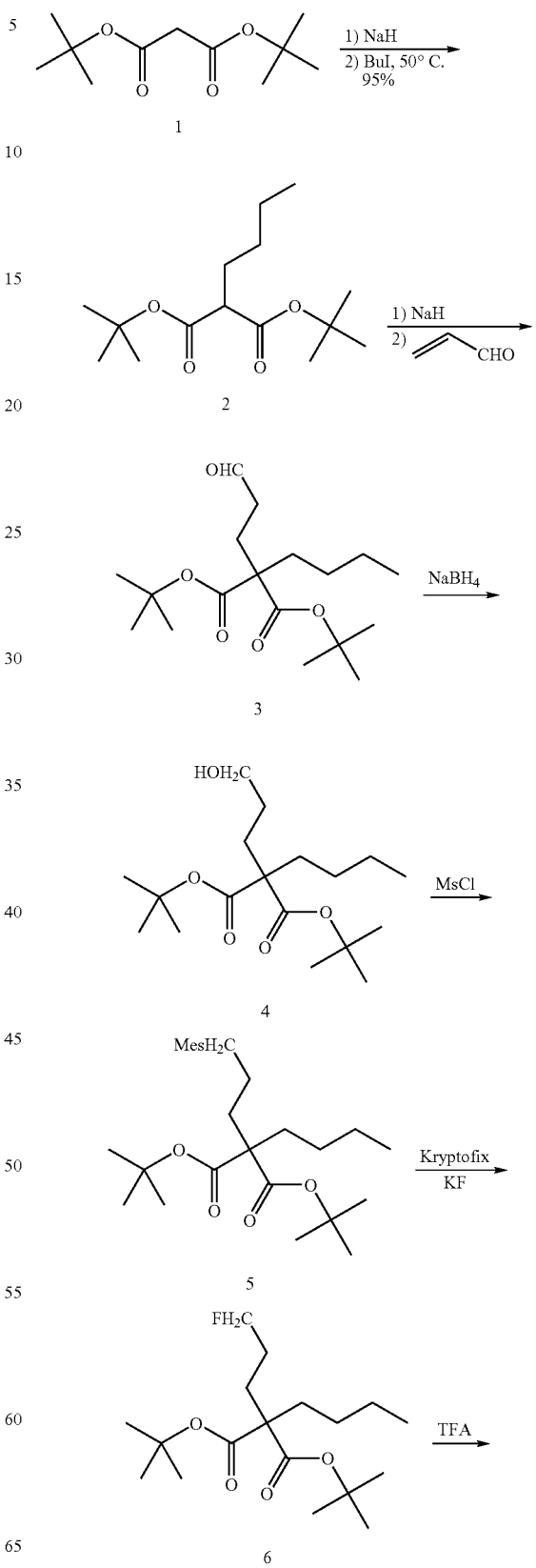

Scheme 1:

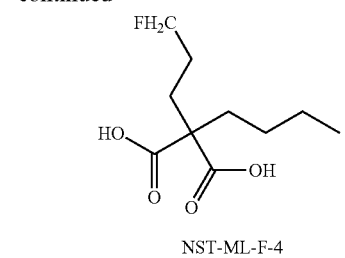

NST-ML-F-4

Example 2

Synthesis of NST-ML-F: 2-methyl-2(3-fluoropropyl)-malonic acid; (Scheme 2)

4-bromo-1-butanol (1), 3 g, was treated with 1.5 eq of 3,4-dihydro-2H-pyran and 0.1 eq of pyridinium para tuloenesulfonate (PPTS) in 135 mL of $CH_2Cl_2$. After work-up and purification, 1.45 g (33%) of product 2 was obtained. 1.0 eq of diethylmethylmalonate was deprotonated with 1 eq of NaH and 1.0 eq of bromide 2 was added along with catalytic amount of KI at 50° C. A complete conversion was observed after 10 hours and a 90% yield was obtained. Deprotection of tetrahydo pyran (THP) with PPTS in ethanol at 55° C. went smoothly. After work-up, a quantitative yield of alcohol 4 was obtained and directly used for the mesylation reaction (as above). With the mesylate 5 in hand, the kryptofix reaction was applied as above. Compound 6 was obtained in 68% yield. Compound 6 (233 mg) was treated with 2 N NaOH/EtOH (30 mL/5 mL) at 50° C. to provide NST-ML-F ca. in 99% yield (190 mg).

The NMR data of the compound are as follows: $^1H$ NMR (300 MHz, $CDCl_3$) δ 11.89 (bs, 2 H), 4.46 (dt, $J_t$=5.9 Hz, $J_d$=47.2 Hz, 2H), 1.99-1.92 (m, 2H), 1.82-1.64 (m, 2H), 1.50 (s, 3H), 1.50-1.40 (m, 2H); $^{13}C$ NMR (75 MHz, $CDCl_3$) δ 178.6, 85.1, 82.9, 54.2, 35.5, 31.0, 30.8, 20.8, 20.7, 20.2; $^{19}F$ NMR (282 MHz, $CDCl_3$) δ −219.0; MS (EI).

Scheme 2:

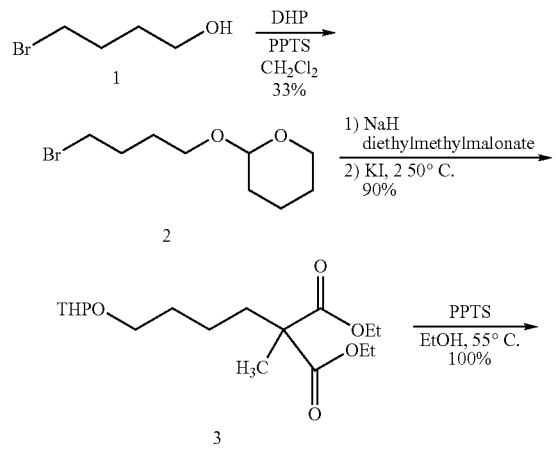

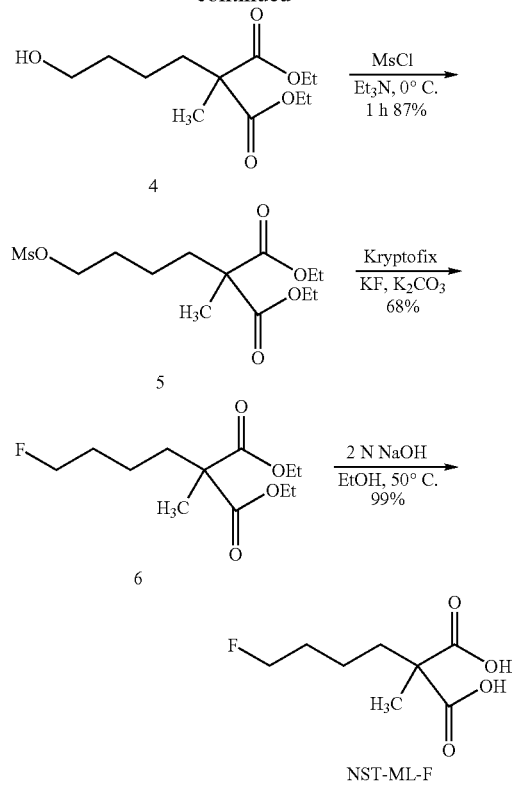

Example 3

Use of Tritium-labeled NST200 for the Detection of Apoptotic Damage following Middle Cerebral Artery Occlusion in Mice Studies were carried-out in adult male Balb/C mice, weighing 20-25 g. Cerebral ischemia was induced by cauterization of the left middle cerebral artery (p-MCA). Briefly, mice were anesthetized, a vertical cut was made and the temporal bone was exposed. Scraping of the temporal bone up to a minimal hole allowed exposure of the artery, subjecting it to further cauterization. Twenty-two hours after the p-MCA cauterization, tritium-labeled NST200 (10 μci in 200 μl saline) was injected intravenously. Two hours later, animals were sacrificed, a blood sample was obtained and brains were removed into liquid nitrogen for further analysis.

Tissue samples were weighted and put into SOLVABLE™ reagent (GNE9100, Packard Biosciences) according to the manufacturer instructions. Briefly, the tissues were incubated with SOLVABLE™, 1 ml for 150 mg tissue. Following 2-4 hours of incubation, extracts were transferred into glass scintillation vials and treated with 30% peroxide, 0.4 ml (and 0.1 M EDTA), for 1 h at 60° C. to avoid color quenching. Ten ml of scintillation liquid (Ultima gold 6013329, Packard Biosciences) was added to each vial and allowed to 1 h of temperature and light adaptation before reading in β counter. The radioactive values were calculated and presented in FIG. 2 as percents of injected dose/g tissue (% ID/g). Statistical analysis included calculation of the ratio of NST200 uptake by the whole damaged versus whole contralateral hemisphere. In addition, calculation of the uptake of the compound by the Region of Interest (ROI) versus non-damaged brain regions was performed, by histopathological assessment of the fraction of the damaged hemisphere, inflicted by the ischemic insult.

Experimental Results

As can be clearly seen from the table presented in FIG. 2 below, the damaged hemisphere showed markedly higher uptake of the radiolabeled NST200, compared with the uptake by the non-damaged control hemisphere, both at one and two hours after injection of the compound. Ratio was about two-fold for the entire hemisphere, and over 6-fold for the Region of Interest (ROI) versus non-damaged brain tissue.

The results obtained in the above model of cerebral ischemia, induced by MCA occlusion demonstrate the ability of the compound of the invention to manifest selective increased uptake in a brain region inflicted by cell death.

Example 4

Selective Binding of Tritium-labeled NST 200 to Cultured Jurkat Cells, Undergoing Apoptosis Induced by CD95.

Cultured Jurkat cells (human adult T cell leukemia cells) were grown in suspension in RPMI medium (Beit-Haemek, Israel), supplemented with 10% fetal calf serum (FCS), 2 mM of L-glutamine, 1 mM of sodium pyruvate, 1 mM 1 mM HEPES and antibiotics (100 units/ml penicilin; 100 µg/ml streptomycin and 12.5 units/ml of nystatin). Prior to induction of apoptosis, medium was replaced with HBS buffer (10 mM HEPES; 140 mM NaCl, 1 mM CaCl). Apoptosis was then triggered by treatment with CD95 (0.1 ug/$10^7$ cells/ml). As a result, a marked percentage of the cells became apoptotic. Non-treated cells served as control. Both control cells and apoptotic cells were then incubated for 40 minutes at room temperature followed by 30 minutes on ice with (2 uCi/$10^7$ cells/0.5 ml) tritium-labeled-labeled NST 200.

After washing the cells twice, 1 ml of SOLVABLE™ reagent (GNE9100, Packard Biosciences) was added to the pellet. Following one hour of incubation at 60° C., the extracts were transferred into glass scintillation vials and 10 ml of scintillation liquid (Ultima gold 6013329, Packard Biosciences) was added to each vial. The radioactivity was counted after 1 hour of cooling to room temperature and dark adaptation. The radioactive values were calculated and presented in percents of total added radiolabeled NST 200.

Experimental Results

Figure 3:
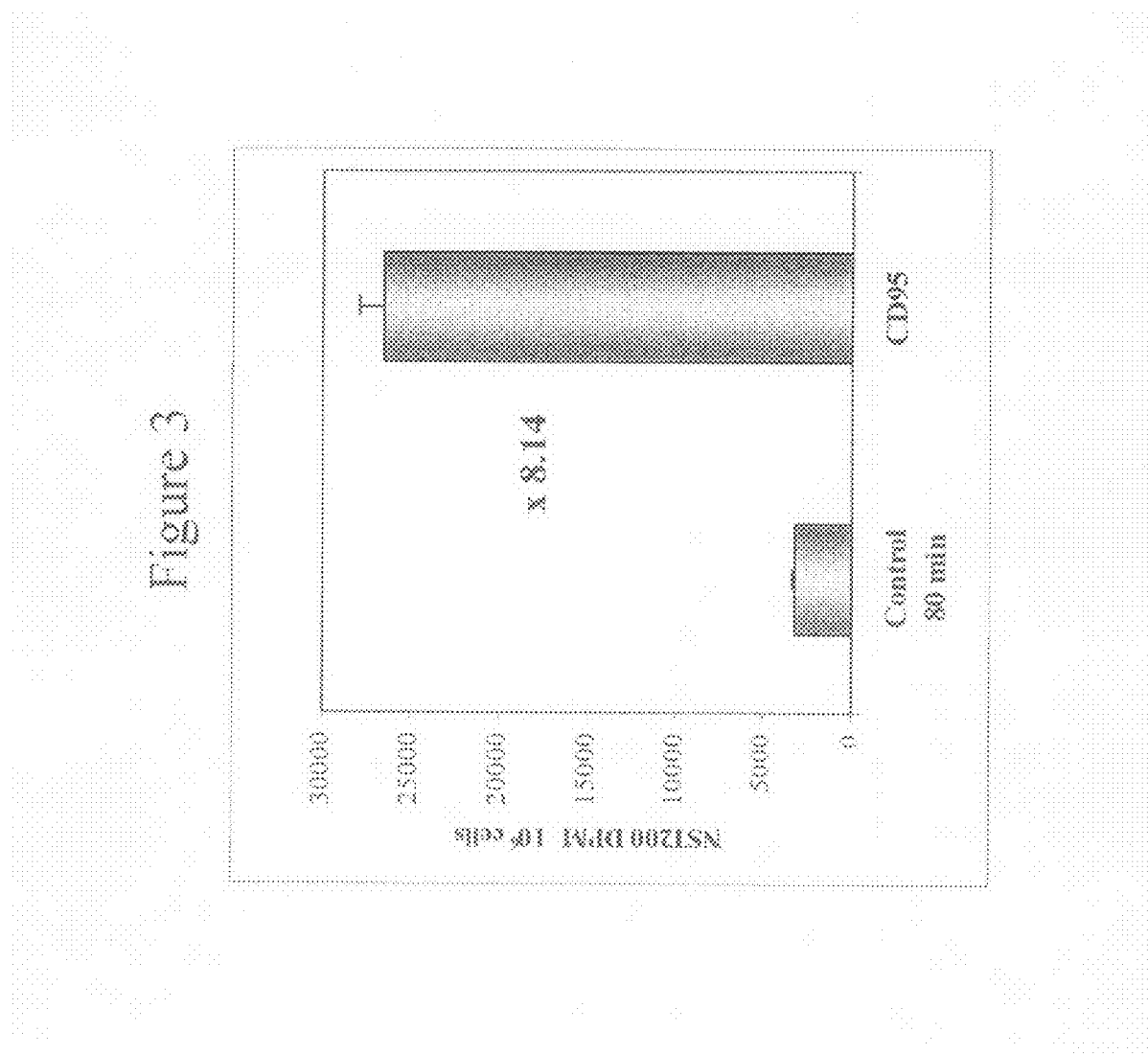
FIG. 3 demonstrates the selective binding of tritium-labeled NST200 to cultured Jurkat cells, undergoing apoptosis induced by CD95.

As can be clearly seen from FIG. 3, the apoptotic cells showed markedly higher uptake of NST200 (over 8 fold) compared to the non-apoptotic cells. The experiment show that NST200 is capable of selective binding to apoptotic cells and can serve as a marker for the detection thereof.

Example 5

Biodistribution of Tritium-labeled NST200 in Melanoma-bearing Mice

Melanoma tumors are characterized by a high level of intrinsic apoptotic load. We have shown, in fluorescent microscopic studies, that the compounds of the invention bind selectively to the cells undergoing cell death within these melanoma tumors while not binding to the viable tumor cells (see Example 7 below). In accordance with these findings, current Example shows biodistribution studies of radio-labeled NST200, and demonstrates that the compound of the invention manifests enhanced uptake by the melanoma tumors comprising foci of cell death in vivo, while binding much less to other organs.

Mouse melanoma cells (B16 F-10) (ATCC CRL-6475) were maintained in DMEM 4.5 gr/l glucose, 4 mM of L-glutamine; 100 units/ml of penicillin; 100 µg/ml of streptomycine; 12.5 units/ml nystatin; and 10% FCS. Cells were grown in flasks trypsinized and seed at a density of 5×$10^6$ cells in 10 ml medium. $C_{57}Bl$ mice (Harlan laboratories, Jerusalem) (5-6 weeks old males) were injected subcutaneous with $10^5$ of B16 F-10 cells in 0.2 ml saline and were examined daily for tumor formation. At day 10, mice were injected intravenously with 10 µci of NST $^3$H-200 in 0.2 ml saline. After one hour, tumors were excised, weighted and tumor lysis was performed using SOLVABLE™ reagent (GNE9100, Packard Bioscience) in a ratio of 1 ml reagent per 150 mg of tumor tissue at 60° C. Following 2-4 hours, 1 ml from each tissue extract was transferred to a glass scintillation vial. To reduce color quenching problems, samples were treated with 0.4 ml of 30% $H_2O_2$ in the presence of 0.066M EDTA. After 15 min of incubation time at room temperature, extracts were incubated for 1 hr at 60° C. and for 15 min in room temperature. Ten ml scintillation liquid (Ultima gold, 6013329, Packard Bioscience) were added to each vial and following 1 hr of incubation and samples were analyzed in a γ-counter (TRI-CARB 2100TR, liquid scintillation analyzer, Packard Bioscience). Values of DPM/g tissue or percents of injected dose (% ID/g tissue) were calculated for each sample.

Experimental Results

The biodistribution data of the tritium-labeled NST200 in the mice with melanoma, one hour post-injection were found to be as set forth in Table 1:

TABLE 1

| Body Organ | % of injected dose/g tissue (average of data from two animals) | Tumor to organ ratio |
| --- | --- | --- |
| Tumor | 1.348 | 1.000 |
| Kidney | 3.139 | 0.429 |
| Heart | 0.569 | 2.367 |
| Liver | 0.204 | 6.594 |
| Muscle | 0.204 | 6.617 |
| Spleen | 0.334 | 4.037 |
| Brain | 0.098 | 13.742 |
| Fat tissue | 0.493 | 3.07 |
| Lung | 0.799 | 1.687 |

As can be seen, the melanoma tumors manifest high level of binding of tritium-labeled NST200 (1.35% of injected dose at one hour after administration). These values were markedly higher than the uptake values by other body organs, with the exception of the kidney, from which clearance of the compound is being performed. These data show that NST200 can serve as a useful tool for detection of cell death within a tumor, manifesting good target/non-target ratios.

Example 6

Selective Binding of NST 203 to Cultured HeLa Cells Undergoing Apoptosis

HeLa S3 cells (ATCC CCL-2.2) were grown in Dulbecco's modified Eagle's medium (DMEM), supplemented with 2 mM of L-glutamine; 100 units/ml of penicillin; 100 µg/ml of streptomycin; 12.5 units/ml of nystatin and 10% of fetal calf serum (FCS). Cells were seeded at a density of $5 \times 10^6$ cells/plate, on a 10 cm$^3$ culture plates, in a volume of 10 ml, and were allowed to age by incubating the culture for 96 hours without exchange of the growth medium. As a result, a marked percentage of the cells became apoptotic. Cells were harvested using a cell scraper, separated to single cells by passage through a syringe with a 18G needle, and re-suspended at a density of $10^6$ cells/ml in PBS buffer at pH=7.4. The selective binding of the NST203 to apoptotic cells is shown in FIG. 4A which demonstrates the uptake of into the population of apoptotic cells (green, glowing color cells, representative are marked by arrows), while not fluorescent is observed in the non-apoptotic cells (blue, not glowing cells, marked by arrow heads).

Figure 4:
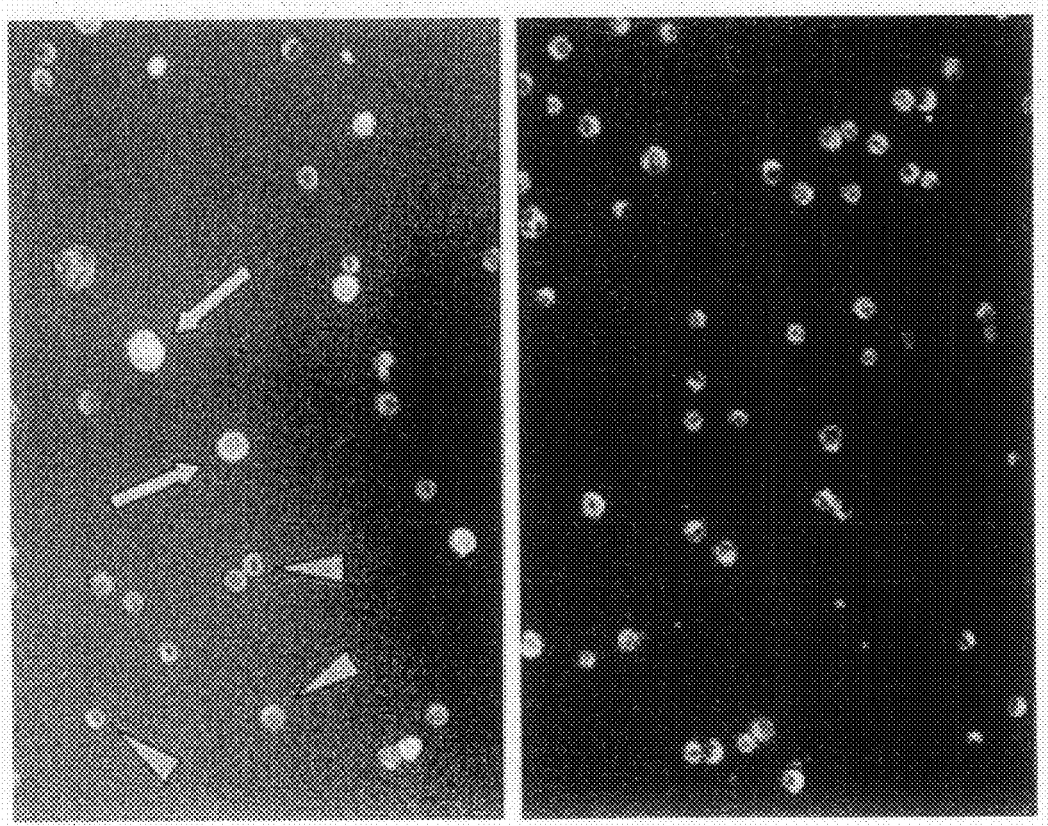
FIG. 4 (A and B) shows fluorescent microscopy, demonstrating the selective binding of NST203 to cultured HeLa cells undergoing apoptosis (FIG. 4A). By contrast, the control compound, n-butyl-dansylamide (BDA), having the same fluorophore but devoid of the NST-ML-Action Motif, did not manifest this selectivity, thus manifesting the activity of the NST-ML-Action Motif in selective binding to the apoptotic cells (FIG. 4B).

By contrast, the control compound n-butyl-dansylamide (BDA), having the same fluorophore but devoid of the NST-ML-Action Motif, did not manifest this selectivity, thus manifesting the activity of the NST-ML-Action Motif in selective binding to the apoptotic cells (FIG. 4B). Therefore, NST203 can serve as a marker, which performs selective binding to apoptotic cells.

Example 7

Selective Binding of NST 203 to Melanoma Cells Undergoing a Death Process induced by Chemotherapy in Mice in vivo.

Experimental Procedures

Mice (c57/black; 8 weeks old male mice) were injected subcutaneously bilaterally, in the flank, with murine melanoma-derived B16-F10 cells (ATCC CRL-6475; $10^5$ cells/mice in a volume of 100 µl). Prior to injection, the cell line was maintained in culture in Dulbecco's modified Eagle's medium (DMEM), supplemented with 4 mM of L-glutamine; 100 units/ml of penicillin; 100 µg/ml of streptomycin; 12.5 units/ml of nystatin and 10% of fetal calf serum (FCS). After 10 days, when tumor diameter reached the size of 5-7 mm, mice were subjected to chemotherapy treatment (Taxol 20 mg/Kg together with Cyclophosphomide, 300 mg/Kg, in a volume of 200 µl intra-peritoneal injection). Twenty-four hours later, NST-203 was injected intravenously, at a dose of 2.8 mg/mouse in 10% chromophore in tris-base buffer. Two hours later, mice were sacrificed and tumors as well as other organs were harvested and immediately frozen in liquid nitrogen. Uptake of NST-203 by the tumors or other organs was assessed by fluorescent microscopy of frozen sections from each tissue.

Experimental Results

Figure 5:
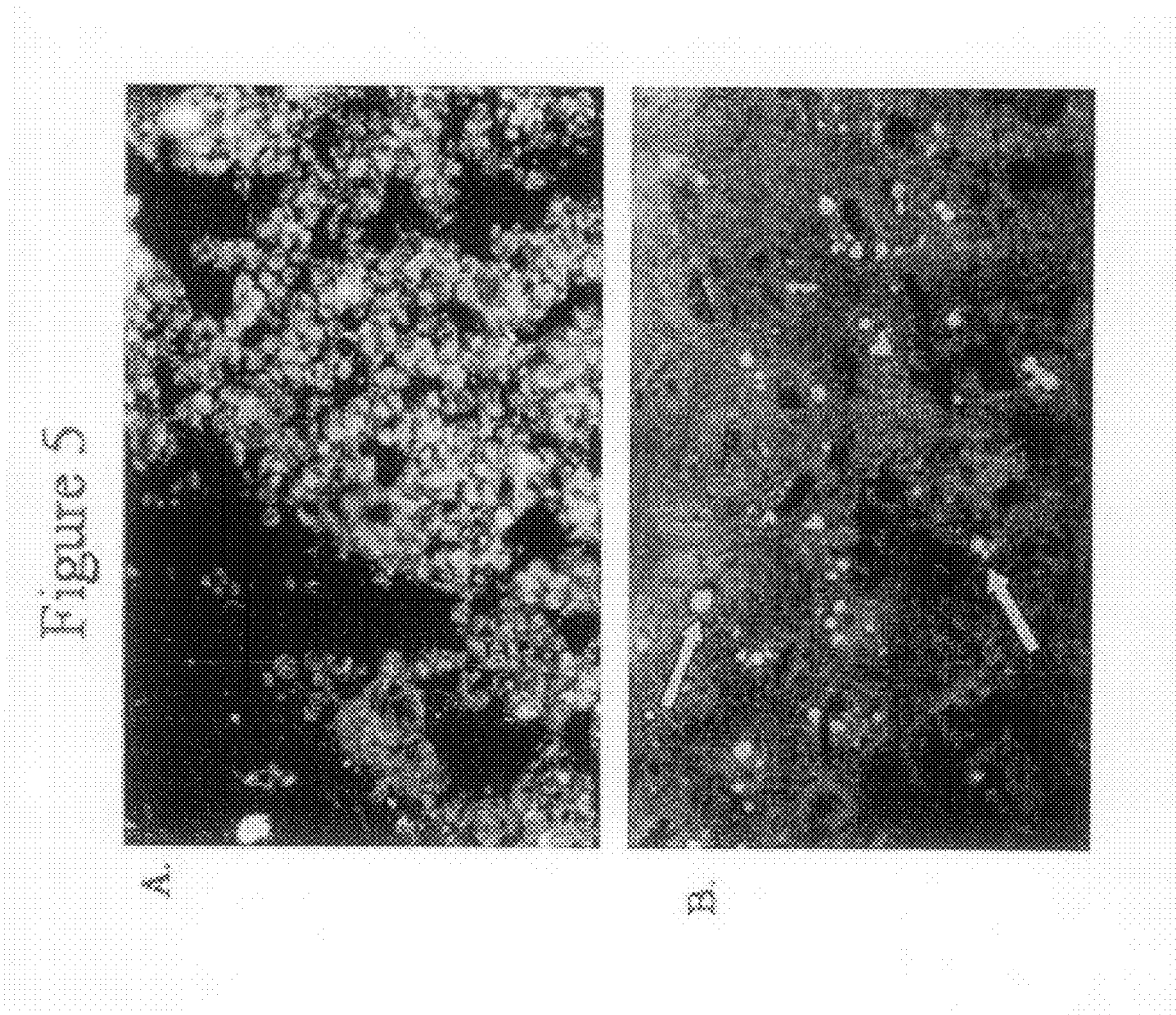
FIG. 5 (A and B) shows fluorescent microscopy of the selective binding of NST203 to cells undergoing cell death induced by chemotherapy in mice in vivo: (A.). Apoptosis of melanoma cells; (B). Apoptosis of epithelial cells of the gastrointestinal tract.

FIG. 5A. shows fluorescent microscopy of the tumor. Extensive binding of NST203 to numerous tumor cells undergoing apoptosis can be observed. Demonstrated are also the intracellular accumulation of the compound (right side of the picture) and the high level of selectivity, reflected by a marked uptake into the apoptotic cells, while the surrounding viable tumor cells remain unstained (left upper side of the picture).

Chemotherapy often acts to induce cell death no only in target tumor tissue, but also in non-target tissues, such as the epithelium of the gastrointestinal tract. FIG. 5B shows the capability of NST203 to selectively detect these cells undergoing apoptosis (see arrows). Similar to the findings in the tumor, viable cells in the gastrointestinal tract did not manifest uptake of NST203 and therefore remained dark.

These results therefore manifest the capability of the compound of the invention, NST203, to target specifically apoptotic cells in vivo, wherein the death process is being induced by chemotherapy. The apoptotic cells are detected in a universal manner, irrespective of the tissue involved. By contrast, viable cells of said tissues do not manifest such binding.

What is claimed is:

1. A method for detecting a PNOM-cell within a cell population, comprising the steps of:
   (i) contacting the cell population with a compound or a conjugate comprising said compound, wherein said compound is represented by the structure as set forth in formula (I):

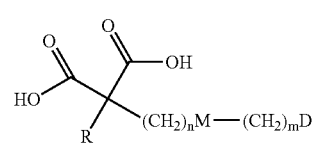

I

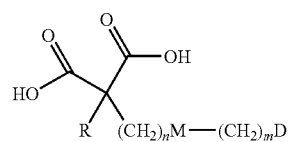

including pharmaceutically acceptable salts, metal chelates, solvates and hydrates of the compound represented by the structure as set forth in formula (I) and solvates and hydrates of the salts; wherein, R represents hydrogen or $C_1$, $C_2$, $C_3$, $C_4$, $C_5$, $C_6$, $C_7$, $C_8$, $C_9$, $C_{10}$, $C_{11}$, $C_{12}C_{13}$, or $C_{14}$ linear or branched alkyl, or combinations thereof;

n and m each stands for an integer of 0, 1, 2, 3 or 4, n and m may be the same or different; M is null; and D is a marker for diagnostics; and wherein said alkylene groups bound to M or D; and, (ii) determining the amount of said compound bound to cells in said cell population, wherein a significant amount of said compound bound to said cells indicates its being a PNOM-cell.

2. A method for detecting a PNOM-cell within a cell population according to claim 1, comprising the steps of:
   (i) contacting the cell population with a compound or a conjugate comprising said compound, wherein said compound is represented by the structure as set forth in the formula:

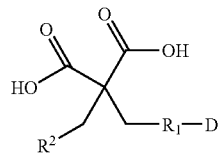

including pharmaceutically acceptable salts, hydrates, solvates and metal chelates, of the compound represented by the structure as set forth in the formula and solvates and hydrates of the salts; wherein, $R_1$ is hydrogen or $C_1$, $C_2$, $C_3$, $C_4$, $C_5$ or $C_6$, linear or branched alkylene; and $R^2$ is hydrogen or $C_1$, $C_2$, $C_3$, $C_4$, $C_5$ or $C_6$ linear or branched alkyl; and D is a marker for imaging;

(ii) determining the amount of said compound bound to cells in said cell population, wherein a significant amount of said compound bound to said cells indicates its being a PNOM-cell.

3. A method according to claim 1, wherein:

said detecting a PNOM cell comprises detecting within a brain of an examined subject;

said contacting comprises administrating a compound or a conjugate comprising said compound to the examined subject, wherein said compound is represented by the structure as set forth in formula (I); and said determining comprises determining the amount of said compound bound to cells in the brain, wherein a significant amount of said compound bound to said cells indicates its being a PNOM-cell.

4. A method according to claim 1, wherein:

said detecting a PNOM cell comprises detecting an apoptotic cell within a tumor or in an organ comprising the tumor in a suspected body area of an examined subject;

said contacting comprises administrating a compound or a conjugate comprising said compound to the examined subject, wherein said compound is represented by the structure as set forth in formula (I); and said determining comprises determining the amount of said compound bound to cells in the tumor or in the organ comprising the tumor, wherein a significant amount of said compound bound to said cells indicates that these tumor cells are undergoing apoptosis.

5. A method according to claim 1, wherein said marker for diagnostics is selected from a marker for imaging or a labeled metal chelate, said marker for imaging is selected from the group consisting of a fluorescent label, a radio-label, a marker for X-ray, a marker for MRI, a marker for PET scan and a label capable of undergoing an enzymatic reaction that produces a detectable color.

6. A method according to claim 1, wherein said marker for diagnostics is a marker for imaging selected from the group consisting of Tc, Tc=O, In, Cu, Ga, Xe, Tl, Re and Re=O, $^{123}$I, $^{131}$I, Gd(III), Fe(III), $Fe_2O_3$, $Fe_3O_4$, Mn(II) $^{18}$F, $^{15}$O, $^{18}$O, $^{11}$C, $^{13}$C, $^{124}$I, $^{13}$N, $^{75}$Br, Tc-99m or In-111.

7. A method for detecting a PNOM-cell within a patient or an animal, comprising the steps of:

(i) administrating a compound or a conjugate comprising said compound, wherein said compound is represented by the structure as set forth in formula (I):

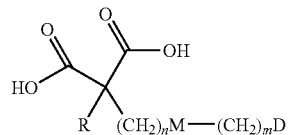

including pharmaceutically acceptable salts, metal chelates, solvates and hydrates of the compound represented by the structure as set forth in formula (I) and solvates and hydrates of the salts; wherein, R represents hydrogen or $C_1$, $C_2$, $C_3$, $C_4$, $C_5$, $C_6$, $C_7$, $C_8$, $C_9$, $C_{10}$, $C_{11}$, $C_{12}$ $C_{13}$, or $C_{14}$ linear or branched alkyl, or combinations thereof;

n and m each stands for an integer of 0, 1, 2, 3 or 4, n and m may be the same or different; M is null; and D is a marker for diagnostics; and wherein said alkylene groups bound to M or D; and (ii) imaging the patient or animal, so as to determine the amount of said compound bound to cells within the patient or animal, wherein a significant amount of said compound bound to said cells indicates its being a PNOM-cell.

8. A method for detecting a PNOM-cell within a patient or an animal according to claim 7, comprising the steps of:

(i) administrating a compound or a conjugate comprising said compound, wherein said compound is represented by the structure as set forth in the formula below:

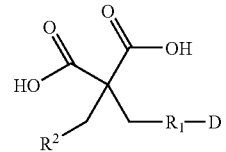

including pharmaceutically acceptable salts, hydrates, solvates and metal chelates, of the compound represented by the structure as set forth in the formula and solvates and hydrates of the salts; wherein, $R^1$ is hydrogen or $C_1$, $C_2$, $C_3$, $C_4$, $C_5$ or $C_6$ linear or branched alkylene; and $R^2$ is hydrogen or $C_1$, $C_2$, $C_3$, $C_4$, $C_5$ or $C_6$ linear or branched alkyl; and D is a marker for imaging;

(ii) imaging the patient or animal, so as to determine the amount of said compound bound to cells within the patient or animal, wherein a significant amount of said compound bound to said cells indicates its being a PNOM-cell.

9. A method according to claim 7 wherein said marker for diagnostics is selected from a marker for imaging or a labeled metal chelate, said marker for imaging is selected from the group consisting of a fluorescent label, a radio-label, a marker for X-ray, a marker for MRI, a marker for PET scan and a label capable of undergoing an enzymatic reaction that produces a detectable color.

10. A method according to claim 7, wherein said marker for diagnostics is a marker for imaging selected from the group consisting of Tc, Tc=O, In, Cu, Ga, Xe, Tl, Re and Re=O, $^{123}$I, $^{131}$I, Gd(III), Fe(III), $Fe_2O_3$, $Fe_3O_4$, Mn(II) $^{18}$F, $^{15}$O, $^{18}$O, $^{11}$C, $^{13}$C, $^{124}$I, $^{13}$N, $^{75}$Br, Tc-99m or In-111.

* * * * *